(12) United States Patent
Rabinovitch et al.

(10) Patent No.: US 8,299,024 B2
(45) Date of Patent: Oct. 30, 2012

(54) METHODS TO RESTORE GLYCEMIC CONTROL

(75) Inventors: Alex Rabinovitch, Edmonton (CA); Wilma L. Suarez-Pinzon, Edmonton (CA)

(73) Assignees: Amylin Pharmaceuticals, LLC, San Diego, CA (US); Eli Lilly and Company, Indianapolis, IN (US)

( * ) Notice: Subject to any disclaimer, the term of this patent is extended or adjusted under 35 U.S.C. 154(b) by 129 days.

(21) Appl. No.: 12/298,933

(22) PCT Filed: May 14, 2007

(86) PCT No.: PCT/US2007/011641
§ 371 (c)(1),
(2), (4) Date: Jan. 7, 2009

(87) PCT Pub. No.: WO2007/133778
PCT Pub. Date: Nov. 22, 2007

(65) Prior Publication Data
US 2009/0203597 A1 Aug. 13, 2009

Related U.S. Application Data

(60) Provisional application No. 60/799,913, filed on May 12, 2006.

(51) Int. Cl.
*A61K 38/16* (2006.01)
*A61K 38/17* (2006.01)

(52) U.S. Cl. .................. 514/6.9; 514/6.7; 514/6.8

(58) Field of Classification Search .................. None
See application file for complete search history.

(56) References Cited

U.S. PATENT DOCUMENTS 5,824,778 A 10/1998 Ishikawa et al.
5,824,784 A 10/1998 Kinstler et al.

OTHER PUBLICATIONS

Kodama et al., Biochemical and Biophysical Research Communications, 327(4):1170-1178, Feb. 2005.*
Xu et al., Diabetes, 48(12):2270-2276, 1999.*
Rother et al., Diabetes Care, 32(12):2251-7, Dec. 2009.*
Buse et al., Diabetes Care, 27(11):2628-2635, 2004.*
Dupre et al., Journal of Clinical Endocrinology & Metabolism, 89(7):3469-3473, 2004.*
Suarez-Pinzon et al., Diabetes, 57:3281-3288, Dec. 2008.*
Bartlett and Landen, *Biorg. Chem.* 14:356-377 (1986).
Eng, J., et al., *J. Biol. Chem.* 265:20259-62 (1990).
Eng, J. et al., *J. Biol. Chem.*, 267:7402-05 (1992).
Forman et al., "ADA Preview: Conference highlights; Jun. 5 conference call" (Jun. 1, 2006) Retrieved from Internet: URL:http://www.wrhambrecht.com/sector/pharm/notes/ir20060601.pdf.
Frias et al., *Curr. Opin. In Endocrinology*, Diabetes and Obesity 14:269-274 (2007).
Goke et al., *J. Biol. Chem.*, 268:19650-55 (1993).
Kodama et al., *Science* 302:1223-27 (2003).
Maki et al., *Proc. Nat'l Acad. Sci. USA* 89:3434-38 (1992).
Ogawa et al., *Diabetes* 53:1700-1705 (2004).
Raufman et al., *J. Biol. Chem.* 267:21432-37 (1992).
Science in the News: "Treating tuberculosis / Reports on smoking / Possible treatment for diabetes", NEWS VOA COM (2003), pp. 1-4 Retrieved from the Internet: https://www.voafanti.com/gate/big5/author.voanews.com/specialenalish/archive/2003-09/a-2003-09-15-5-1.cfm.
Sharma et al., *Diabetologia* 49:1247-1253 (2006).
Suarez-Pinzon et al., *Diabetes* 54:2596-601 (2005).
Suarez-Pinzon et al., *Diabetes* 55:A363 (Jun. 2006).
Tourrel et al., *Diabetes* 51:1443-1452 (2002).
Trautmann et al., MacConell et al., *Diabetologia* (2007, Supplement 1) / Minutes of the 42nd General Assembly of the European Association for the Study of Diabetes, Copenhagen, Sep. 2006, vol. 50, Sep. 2007, p. S1, S338, S351.
Waterman, *Bull. Math. Biol.* 46:473 (1984).
Lampeter, E.F. et al., "Lessons from the NOD mouse for the pathogenesis and immunotherapy of human type 1 (insulin-dependent) diabetes mellitus", Diabetologia (1989) 32:703-708.

* cited by examiner

*Primary Examiner* — Marianne P Allen
(74) *Attorney, Agent, or Firm* — Kilpatrick Townsend & Stockton LLP

(57) ABSTRACT

Provided herein are methods and compositions to achieve a sustained delay in the progression of, or an amelioration of diabetes in a subject, or a delay in diabetes onset in a subject at risk for diabetes, comprising an abbreviated course of administration of a pharmaceutical composition comprising an exendin or an exendin agonist analog in an amount effective to induce cell regeneration.

5 Claims, 8 Drawing Sheets

```
                          SEQUENCE LISTING

<160> NUMBER OF SEQ ID NOS: 37

<210> SEQ ID NO 1
<211> LENGTH: 39
<212> TYPE: PRT
<213> ORGANISM: Heloderma suspectum
<220> FEATURE:
<223> OTHER INFORMATION: C-term amidated

<400> SEQUENCE: 1

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 2
<211> LENGTH: 39
<212> TYPE: PRT
<213> ORGANISM: Heloderma horridum
<220> FEATURE:
<223> OTHER INFORMATION: C-term amidated

<400> SEQUENCE: 2

His Ser Asp Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Pro Pro Pro Ser
         35

<210> SEQ ID NO 3
<211> LENGTH: 30
<212> TYPE: PRT
<213> ORGANISM: Homo sapiens
<220> FEATURE:
<223> OTHER INFORMATION: C-term amidated

<400> SEQUENCE: 3

His Ala Glu Gly Thr Phe Thr Ser Asp Val Ser Ser Tyr Leu Glu Gly
  1               5                  10                  15

Gln Ala Ala Lys Glu Phe Ile Ala Trp Leu Val Lys Gly Arg
             20                  25                  30

<210> SEQ ID NO 4
<211> LENGTH: 31
<212> TYPE: PRT
<213> ORGANISM: Heloderma sp.
<220> FEATURE:
<223> OTHER INFORMATION: C-term amidated

<400> SEQUENCE: 4

Asp Leu Ser Lys Gln Met Glu Glu Glu Ala Val Arg Leu Phe Ile Glu
  1               5                  10                  15

Trp Leu Lys Asn Gly Gly Pro Ser Ser Gly Ala Pro Pro Pro Ser
```

-continued

```
                    20                  25                  30

<210> SEQ ID NO 5
<211> LENGTH: 38
<212> TYPE: PRT
<213> ORGANISM: Heloderma sp.

<400> SEQUENCE: 5

His Ser Asp Ala Thr Phe Thr Ala Glu Tyr Ser Lys Leu Leu Ala Lys
 1               5                  10                  15

Leu Ala Leu Gln Lys Tyr Leu Glu Ser Ile Leu Gly Ser Ser Thr Ser
                20                  25                  30

Pro Arg Pro Pro Ser Ser
            35

<210> SEQ ID NO 6
<211> LENGTH: 37
<212> TYPE: PRT
<213> ORGANISM: Heloderma sp.

<400> SEQUENCE: 6

His Ser Asp Ala Thr Phe Thr Ala Glu Tyr Ser Lys Leu Leu Ala Lys
 1               5                  10                  15

Leu Ala Leu Gln Lys Tyr Leu Glu Ser Ile Leu Gly Ser Ser Thr Ser
                20                  25                  30

Pro Arg Pro Pro Ser
            35

<210> SEQ ID NO 7
<211> LENGTH: 35
<212> TYPE: PRT
<213> ORGANISM: Heloderma sp.
<220> FEATURE:
<223> OTHER INFORMATION: C-term amidated

<400> SEQUENCE: 7

His Ser Asp Ala Ile Phe Thr Glu Glu Tyr Ser Lys Leu Leu Ala Lys
 1               5                  10                  15

Leu Ala Leu Gln Lys Tyr Leu Ala Ser Ile Leu Gly Ser Arg Thr Ser
                20                  25                  30

Pro Pro Pro
        35

<210> SEQ ID NO 8
<211> LENGTH: 35
<212> TYPE: PRT
<213> ORGANISM: Heloderma sp.
<220> FEATURE:
<223> OTHER INFORMATION: C-term amidated

<400> SEQUENCE: 8

His Ser Asp Ala Ile Phe Thr Gln Gln Tyr Ser Lys Leu Leu Ala Lys
 1               5                  10                  15

Leu Ala Leu Gln Lys Tyr Leu Ala Ser Ile Leu Gly Ser Arg Thr Ser
                20                  25                  30

Pro Pro Pro
        35

<210> SEQ ID NO 9
<211> LENGTH: 30
<212> TYPE: PRT
<213> ORGANISM: Heloderma sp.
```

```
<400> SEQUENCE: 9

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 10
<211> LENGTH: 30
<212> TYPE: PRT
<213> ORGANISM: Heloderma sp.
<220> FEATURE:
<223> OTHER INFORMATION: C-term amidated

<400> SEQUENCE: 10

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly
            20                  25                  30

<210> SEQ ID NO 11
<211> LENGTH: 28
<212> TYPE: PRT
<213> ORGANISM: Heloderma sp.
<220> FEATURE:
<223> OTHER INFORMATION: C-term amidated

<400> SEQUENCE: 11

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn
            20                  25

<210> SEQ ID NO 12
<211> LENGTH: 39
<212> TYPE: PRT
<213> ORGANISM: Heloderma sp.
<220> FEATURE:
<223> OTHER INFORMATION: C-term amidated

<400> SEQUENCE: 12

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn Gly Gly Pro Ser
            20                  25                  30

Ser Gly Ala Pro Pro Ser
            35

<210> SEQ ID NO 13
<211> LENGTH: 28
<212> TYPE: PRT
<213> ORGANISM: Heloderma sp.
<220> FEATURE:
<223> OTHER INFORMATION: C-term amidated

<400> SEQUENCE: 13

His Gly Glu Gly Thr Phe Thr Ser Asp Leu Ser Lys Gln Leu Glu Glu
 1               5                  10                  15

Glu Ala Val Arg Leu Phe Ile Glu Phe Leu Lys Asn
            20                  25

<210> SEQ ID NO 14
<211> LENGTH: 28
<212> TYPE: PRT
<213> ORGANISM: Heloderma sp.
```

```
<220> FEATURE:
<223> OTHER INFORMATION: C-term amidated

<400> SEQUENCE: 14

His Gly Glu Gly Thr Phe Thr Ser Asp Leu Ser Lys Gln Leu Glu Glu
 1               5                  10                  15

Glu Ala Val Arg Leu Ala Ile Glu Phe Leu Lys Asn
                20                  25

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
```

```
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Ala, Phe, Tyr or naphthylalanine
<220> FEATURE:
<221> NAME/KEY: MOD_RES
<222> LOCATION: (23)
<223> OTHER INFORMATION: Ile, Val, Leu, pentylglycine,
      tert-butylglycine or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 15

Xaa Xaa Xaa Gly Xaa Xaa Xaa Xaa Xaa Xaa Xaa Xaa Xaa Xaa Xaa Xaa
  1               5                  10                  15

Xaa Ala Xaa Xaa Xaa Xaa Xaa Xaa Xaa Xaa Xaa Xaa Gly Gly Xaa Ser
                 20                  25                  30

Ser Gly Ala Xaa Xaa Xaa
             35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)
<223> OTHER INFORMATION: His, Arg, Tyr, Ala, Norval, Val or Norleu
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (4)
<223> OTHER INFORMATION: Ala, Norval, Val, Norleu or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Ala, Norval, Val, Norleu, Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
```

```
<223> OTHER INFORMATION: Ile, Val, Leu, pentylglycine,
      tert-butylglycine or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (39)
<223> OTHER INFORMATION: Ser, Tyr or not present
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 16

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa Xaa
         35

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His or Arg
<220> FEATURE:
<221> NAME/KEY: MOD_RES
<222> LOCATION: (2)
<223> OTHER INFORMATION: Gly or Ala
<220> FEATURE:
```

```
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu or pentylglycine
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu or pentylglycine
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe or naphthylalanine
<220> FEATURE:
<221> NAME/KEY: MOD_RES
<222> LOCATION: (23)
<223> OTHER INFORMATION: Ile, Val or tert-butylglycine
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp or Phe
<220> FEATURE:
<221> NAME/KEY: MOD_RES
<222> LOCATION: (26)
<223> OTHER INFORMATION: Ala or Leu
<220> FEATURE:
```

```
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, thioproline, N-methylalanine
      or not present
<220> FEATURE:
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, thioproline, N-methylalanine
      or not present
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 17

Xaa Xaa Xaa Gly Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 18
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His or Ala
<220> FEATURE:
<221> NAME/KEY: MOD_RES
<222> LOCATION: (2)
<223> OTHER INFORMATION: Gly or Ala
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (4)
<223> OTHER INFORMATION: Ala or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
```

```
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Ala, Asp or Glu
<220> FEATURE:
<221> NAME/KEY: MOD_RES
<222> LOCATION: (10)
<223> OTHER INFORMATION: Ala, Leu or pentylglycine
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Met or pentylglycine
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala or Leu
<220> FEATURE:
<221> NAME/KEY: MOD_RES
<222> LOCATION: (22)
<223> OTHER INFORMATION: Phe or naphthylalanine
<220> FEATURE:
<221> NAME/KEY: MOD_RES
<222> LOCATION: (23)
<223> OTHER INFORMATION: Ile, Val or tert-butylglycine
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp or Phe
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)
<223> OTHER INFORMATION: Ala or Lys
<220> FEATURE:
<221> NAME/KEY: MOD_RES
<222> LOCATION: (28)
<223> OTHER INFORMATION: Ala or Asn
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, thioproline, N-methylalanine
      or not present
<220> FEATURE:
```

```
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, thioproline, N-methylalanine
      or not present
<220> FEATURE:
<221> NAME/KEY: MOD_RES
<222> LOCATION: (39)
<223> OTHER INFORMATION: May or may not be present
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 18

Xaa Xaa Xaa Xaa Xaa Xaa Xaa Xaa Xaa Xaa Xaa Xaa Xaa Xaa Xaa Xaa
 1               5                  10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa Ser
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, Tyr or 4-imidazopropionyl
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
```

```
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala, Leu or Lys
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine,
      tert-butylglycine or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)..(28)
<223> OTHER INFORMATION: Lys, Asn or Ala
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 19

Xaa Xaa Xaa Gly Xaa Xaa Xaa Xaa Xaa Xaa Xaa Xaa Xaa Xaa Xaa Xaa
 1               5                  10                  15
```

```
Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
            35
```

```
<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, Tyr, Ala, Norval, Val, Norleu
      or 4-imidazopropionyl
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Ala, Asp or Glu
<220> FEATURE:
<221> NAME/KEY: MOD_RES
<222> LOCATION: (4)
<223> OTHER INFORMATION: Ala, Norval, Val, Norleu or Gly
<220> FEATURE:
<221> NAME/KEY: MOD_RES
<222> LOCATION: (5)
<223> OTHER INFORMATION: Ala or Thr
<220> FEATURE:
<221> NAME/KEY: MOD_RES
<222> LOCATION: (6)
<223> OTHER INFORMATION: Ala, Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ala, Ser or Thr
<220> FEATURE:
<221> NAME/KEY: MOD_RES
<222> LOCATION: (9)
<223> OTHER INFORMATION: Ala, Norval, Val, Norleu, Asp or Glu
<220> FEATURE:
<221> NAME/KEY: MOD_RES
<222> LOCATION: (10)
<223> OTHER INFORMATION: Ala, Leu, Ile, Val, pentylglycine or Met
<220> FEATURE:
<221> NAME/KEY: MOD_RES
<222> LOCATION: (11)
<223> OTHER INFORMATION: Ala or Ser
<220> FEATURE:
<221> NAME/KEY: MOD_RES
<222> LOCATION: (12)
<223> OTHER INFORMATION: Ala or Lys
<220> FEATURE:
<221> NAME/KEY: MOD_RES
<222> LOCATION: (13)
<223> OTHER INFORMATION: Ala or Gln
<220> FEATURE:
<221> NAME/KEY: MOD_RES
<222> LOCATION: (14)
<223> OTHER INFORMATION: Ala, Leu, Ile, pentylglycine, Val or Met
<220> FEATURE:
<221> NAME/KEY: MOD_RES
<222> LOCATION: (15)..(17)
<223> OTHER INFORMATION: Ala or Glu
<220> FEATURE:
<221> NAME/KEY: MOD_RES
<222> LOCATION: (19)
<223> OTHER INFORMATION: Ala or Val
```

```
<220> FEATURE:
<221> NAME/KEY: MOD_RES
<222> LOCATION: (20)
<223> OTHER INFORMATION: Ala or Arg
<220> FEATURE:
<221> NAME/KEY: MOD_RES
<222> LOCATION: (21)
<223> OTHER INFORMATION: Ala, Leu or Lys
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine,
     tert-butylglycine or Met
<220> FEATURE:
<221> NAME/KEY: MOD_RES
<222> LOCATION: (24)
<223> OTHER INFORMATION: Ala, Glu or Asp
<220> FEATURE:
<221> NAME/KEY: MOD_RES
<222> LOCATION: (25)
<223> OTHER INFORMATION: Ala, Trp, Phe, Tyr or naphthylalanine
<220> FEATURE:
<221> NAME/KEY: MOD_RES
<222> LOCATION: (26)
<223> OTHER INFORMATION: Ala or Leu
<220> FEATURE:
<221> NAME/KEY: MOD_RES
<222> LOCATION: (27)..(28)
<223> OTHER INFORMATION: Lys, Asn or Ala
<220> FEATURE:
<221> NAME/KEY: MOD_RES
<222> LOCATION: (29)..(30)
<223> OTHER INFORMATION: May or may not be present
<220> FEATURE:
<221> NAME/KEY: MOD_RES
<222> LOCATION: (31)
<223> OTHER INFORMATION: Pro, homoproline, 3Hyp, 4Hyp, thioproline,
     N-alkylglycine, N-alkylpentylglycine,
     N-alkylalanine or not present
<220> FEATURE:
<221> NAME/KEY: MOD_RES
<222> LOCATION: (32)..(35)
<223> OTHER INFORMATION: May or may not be present
<220> FEATURE:
<221> NAME/KEY: MOD_RES
<222> LOCATION: (36)..(38)
<223> OTHER INFORMATION: Pro, homoproline, 3Hyp, 4Hyp, thioproline,
     N-alkylglycine, N-alkylpentylglycine,
     N-alkylalanine or not present
<220> FEATURE:
<221> NAME/KEY: MOD_RES
<222> LOCATION: (39)
<223> OTHER INFORMATION: Ser, Tyr or not present
<220> FEATURE:
<223> OTHER INFORMATION: May or may not be C-term amidated
<220> FEATURE:
<223> OTHER INFORMATION: See specification as filed for detailed
     description of substitutions and preferred embodiments

<400> SEQUENCE: 20

Xaa Xaa Xaa Xaa Xaa Xaa Xaa Xaa Xaa Xaa Xaa Xaa Xaa Xaa Xaa Xaa
 1               5                   10                  15

Xaa Ala Xaa Xaa Xaa Xaa Xaa Xaa Xaa Xaa Xaa Xaa Gly Gly Xaa Ser
             20                  25                  30

Ser Gly Ala Xaa Xaa Xaa Xaa
         35

<210> SEQ ID NO 21
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Asp or Glu
<220> FEATURE:
<221> NAME/KEY: MOD_RES
<222> LOCATION: (6)
<223> OTHER INFORMATION: Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine or Met
<220> FEATURE:
<221> NAME/KEY: MOD_RES
<222> LOCATION: (14)
<223> OTHER INFORMATION: Leu, Ile, pentylglycine, Val or Met
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine,
      tert-butylglycine or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr or naphthylalanine
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (39)
<223> OTHER INFORMATION: Ser, Thr or Tyr
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 21

Xaa Xaa Xaa Gly Thr Xaa Xaa Xaa Xaa Xaa Ser Lys Gln Xaa Glu Glu
```

```
            1               5              10              15
Glu Ala Val Arg Leu Xaa Xaa Xaa Xaa Leu Lys Asn Gly Gly Xaa Ser
                20                  25                  30

Ser Gly Ala Xaa Xaa Xaa Xaa
            35

<210> SEQ ID NO 22
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: His, Arg, Tyr or 4-imidazopropionyl
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Asp or Glu
<220> FEATURE:
<221> NAME/KEY: MOD_RES
<222> LOCATION: (6)
<223> OTHER INFORMATION: Phe, Tyr or naphthylalanine
<220> FEATURE:
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine or Met
<220> FEATURE:
<221> NAME/KEY: MOD_RES
<222> LOCATION: (14)
<223> OTHER INFORMATION: Leu, Ile, pentylglycine, Val or Met
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine,
      tert-butylglycine or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr or naphthylalanine
<220> FEATURE:
<221> NAME/KEY: MOD_RES
<222> LOCATION: (27)..(28)
<223> OTHER INFORMATION: Lys or Asn
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
```

```
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine,
      N-alkylalanine or not present
<220> FEATURE:
<221> NAME/KEY: MOD_RES
<222> LOCATION: (39)
<223> OTHER INFORMATION: Ser, Thr or Tyr
<220> FEATURE:
<223> OTHER INFORMATION: May or may not be C-term amidated
<220> FEATURE:
<223> OTHER INFORMATION: See specification as filed for detailed
      description of substitutions and preferred embodiments

<400> SEQUENCE: 22

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Xaa Xaa Gly Gly Xaa Ser
             20                  25                  30

Ser Gly Ala Xaa Xaa Xaa Xaa
             35

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine,
      N-alkylalanine
<220> FEATURE:
<223> OTHER INFORMATION: May or may not be C-term amidated

<400> SEQUENCE: 23

Gly Gly Xaa Ser Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine,
      N-alkylalanine
<220> FEATURE:
<223> OTHER INFORMATION: May or may not be C-term amidated

<400> SEQUENCE: 24

Gly Gly Xaa Ser Ser Gly
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)
<223> OTHER INFORMATION: Pro, homoproline, 3Hyp, 4Hyp, thioproline,
      N-alkylglycine, N-alkylpentylglycine,
      N-alkylalanine
<220> FEATURE:
<223> OTHER INFORMATION: May or may not be C-term amidated

<400> SEQUENCE: 25

Gly Gly Xaa Ser Ser Gly Ala
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine,
      N-alkylalanine
<220> FEATURE:
<221> NAME/KEY: MOD_RES
<222> LOCATION: (8)
<223> OTHER INFORMATION: Pro, homoproline, 3Hyp, 4Hyp, thioproline,
      N-alkylglycine, N-alkylpentylglycine,
      N-alkylalanine
<220> FEATURE:
<223> OTHER INFORMATION: May or may not be C-term amidated

<400> SEQUENCE: 26

Gly Gly Xaa Ser Ser Gly Ala Xaa
  1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine,
      N-alkylalanine
<220> FEATURE:
<221> NAME/KEY: MOD_RES
<222> LOCATION: (8)..(9)
<223> OTHER INFORMATION: Pro, homoproline, 3Hyp, 4Hyp, thioproline,
      N-alkylglycine, N-alkylpentylglycine,
      N-alkylalanine
<220> FEATURE:
<223> OTHER INFORMATION: May or may not be C-term amidated

<400> SEQUENCE: 27

Gly Gly Xaa Ser Ser Gly Ala Xaa Xaa
  1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
```

```
        N-alkylglycine, N-alkylpentylglycine,
        N-alkylalanine
<220> FEATURE:
<221> NAME/KEY: MOD_RES
<222> LOCATION: (8)..(10)
<223> OTHER INFORMATION: Pro, homoproline, 3Hyp, 4Hyp, thioproline,
        N-alkylglycine, N-alkylpentylglycine,
        N-alkylalanine
<220> FEATURE:
<223> OTHER INFORMATION: May or may not be C-term amidated

<400> SEQUENCE: 28

Gly Gly Xaa Ser Ser Gly Ala Xaa Xaa Xaa
 1               5                  10

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<223> OTHER INFORMATION: May or may not be C-term amidated

<400> SEQUENCE: 29

Gly Gly Xaa Ser Ser
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<223> OTHER INFORMATION: May or may not be C-term amidated

<400> SEQUENCE: 30

Gly Gly Xaa Ser Ser Gly
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: MOD_RES
<222> LOCATION: (3)
<223> OTHER INFORMATION: Pro, homoproline, thioproline, N-methylalanine
<220> FEATURE:
<223> OTHER INFORMATION: May or may not be C-term amidated

<400> SEQUENCE: 31

Gly Gly Xaa Ser Ser Gly Ala
 1               5

<210> SEQ ID NO 32
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<221> NAME/KEY: MOD_RES
<222> LOCATION: (8)
<223> OTHER INFORMATION: Pro, homoproline, thioproline, N-methylalanine
<220> FEATURE:
<223> OTHER INFORMATION: May or may not be C-term amidated

<400> SEQUENCE: 32

Gly Gly Xaa Ser Ser Gly Ala Xaa
 1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<221> NAME/KEY: MOD_RES
<222> LOCATION: (8)..(9)
<223> OTHER INFORMATION: Pro, homoproline, thioproline, N-methylalanine
<220> FEATURE:
<223> OTHER INFORMATION: May or may not be C-term amidated

<400> SEQUENCE: 33

Gly Gly Xaa Ser Ser Gly Ala Xaa Xaa
 1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<221> NAME/KEY: MOD_RES
<222> LOCATION: (8)..(10)
<223> OTHER INFORMATION: Pro, homoproline, thioproline, N-methylalanine
<220> FEATURE:
<223> OTHER INFORMATION: May or may not be C-term amidated

<400> SEQUENCE: 34

Gly Gly Xaa Ser Ser Gly Ala Xaa Xaa Xaa
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, 3Hyp, 4Hyp, thioproline,
      N-alkylglycine, N-alkylpentylglycine,
```

-continued

```
         N-alkylalanine
<220> FEATURE:
<221> NAME/KEY: MOD_RES
<222> LOCATION: (8)..(10)
<223> OTHER INFORMATION: Pro, homoproline, 3Hyp, 4Hyp, thioproline,
      N-alkylglycine, N-alkylpentylglycine,
      N-alkylalanine
<220> FEATURE:
<221> NAME/KEY: MOD_RES
<222> LOCATION: (11)
<223> OTHER INFORMATION: Ser or Tyr
<220> FEATURE:
<223> OTHER INFORMATION: May or may not be C-term amidated

<400> SEQUENCE: 35

Gly Gly Xaa Ser Ser Gly Ala Xaa Xaa Xaa Xaa
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<221> NAME/KEY: MOD_RES
<222> LOCATION: (8)..(10)
<223> OTHER INFORMATION: Pro, homoproline, thioproline, N-methylalanine
<220> FEATURE:
<221> NAME/KEY: MOD_RES
<222> LOCATION: (11)
<223> OTHER INFORMATION: Ser or Tyr
<220> FEATURE:
<223> OTHER INFORMATION: May or may not be C-term amidated

<400> SEQUENCE: 36

Gly Gly Xaa Ser Ser Gly Ala Xaa Xaa Xaa Xaa
 1               5                  10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pro, homoproline, thioproline, N-methylalanine
<220> FEATURE:
<221> NAME/KEY: MOD_RES
<222> LOCATION: (8)..(10)
<223> OTHER INFORMATION: Pro, homoproline, thioproline, N-methylalanine
<220> FEATURE:
<223> OTHER INFORMATION: May or may not be C-term amidated

<400> SEQUENCE: 37

Gly Gly Xaa Ser Ser Gly Ala Xaa Xaa Xaa Ser
 1               5                  10
```

METHODS TO RESTORE GLYCEMIC CONTROL

RELATED APPLICATIONS

This application is a §371 of PCT/US2007/011641 filed May 14, 2007, which claims priority to U.S. Provisional Application No. 60/799,913 filed May 12, 2006.

FIELD OF THE INVENTION

The present invention relates to the fields of medicine and health. More particularly, the present invention relates to methods and compositions restore glycemic control in subjects, for example, subjects with diabetes.

BACKGROUND OF THE INVENTION

Diabetes mellitus is characterized by insufficiency of the pancreatic β cells to maintain normal levels of blood glucose or normoglycemia. Under normal conditions, pancreatic β cells secrete insulin (as well as other hormones) in response to an increased blood glucose level, e.g., after a meal. Insulin acts to lower blood glucose levels through actions that include stimulation of fat synthesis, promotion of triglyceride storage in fat cells, and promotion of protein synthesis in the liver and muscle. In diabetes, the inability to maintain normoglycemia results from a failure of the pancreatic β cells to produce insulin, the development of insulin resistance in tissues that typically participate in blood glucose regulation, or some combination of these. The subsequent hyperglycemia contributes significantly to an increased risk of cardiovascular disease, neuropathy, nephropathy, retinopathy, hypertension, dyslipidemia, as well as increased morbidity and mortality.

In most patients with type I diabetes, pancreatic β cells are destroyed by an autoimmune response that can result in an absolute deficiency in insulin production. While some patients lack evidence of an autoimmune response against pancreatic β cells (known as idiopathic type 1 diabetics), the absence of pancreatic β cell still manifests itself as a deficiency in insulin production. Current treatments for type 1 diabetics include insulin injections as well as pancreatic β cell transplantation. Such therapies are risky and often unsuccessful. For example, it is difficult to regulate blood glucose with insulin rejections, and thus bouts of hypoglycemia are not uncommon. Insulin also frequently results in weight gain for the patient. Pancreatic islet transplantation carries all the risks associated with any organ transplantation which include side effects associated with the required immunosuppressive therapies to avoid transplant rejection. Finally, type I diabetes is most common is children and adolescents with an estimated 500,000 to 1 million type I diabetics in the United States alone.

Thus, it is urgent, unmet need for new methods of stimulating pancreatic β cell regeneration in the treatment of diabetes.

SUMMARY OF THE INVENTION

Provided herein are methods for inducing pancreatic β cell regeneration comprising administering to a subject in need thereof, a pharmaceutical composition comprising an exendin or an exendin agonist analog in an amount effective to restore normoglycemia, wherein said exendin or exendin agonist analog is administered over a short duration and said effective amount is from about 3 μg/kg to less than about 100 μg/kg. In one embodiment, the subject has early onset type I diabetes. In one embodiment, the subject has type I diabetes. In some embodiments the effective amount is from about 10 μg/kg to less than about 30 μg/kg.

Further provided herein are methods to achieve a sustained delay in the progression of, or an amelioration of diabetes in a subject, or a delay in diabetes onset in a subject at risk for diabetes, comprising an abbreviated course of administration of a pharmaceutical composition comprising an exendin or an exendin agonist analog in an amount effective to induce β cell regeneration. In one embodiment, the subject has type I diabetes. In some embodiments, the delay in diabetes progression or the amelioration of diabetes occurs in the absence of immunosuppressive therapy. In one embodiment, the effective amount is about 3 μg/kg to less than about 100 μg/kg twice a day (BID). In some embodiments the effective amount is from about 10 μg/kg to less than about 30 μg/kg twice a day. In other embodiments the effective amount is from about 3 μg/kg to less than about 30 μg/kg twice a day.

In some embodiments, the exendin is exendin-4. In some embodiment, the exendin agonist analog is a peptide compound of Formula I, Formula II, Formula III, Formula IV, Formula V, Formula VI or Formula VII.

In some embodiments, pancreatic insulin content is restored by at least 5%, at least 10%, at least 15%, at least 20%, at least 25%, at least 30%, at least 40%, at least 50%, at least 60%, at least 70%, at least 80%, at least 90%, at least 95%, or at least 100%.

In some embodiments, the ameriolation of diabetes (e.g., achieving normoglycemia) after the cessation of exendin or exendin agonist analog treatment is for at least 1 week, at least 2 weeks, at least 3 weeks, at least 1 month, at least 2 months, at least 3 months, at least 4 months, at least 5 months, at least 6 months, or at least 1 year.

In some embodiments, the sustained delay in the progression of diabetes is for at least 1 month, at least 2 months, at least 3 months, at least 4 months, at least 5 months, at least 6 months, at least 1 year, at least 18 months, or at least 2 years.

In other embodiments, $HbA_{1c}$ is reduced by at least 0.5%, at least 1.0%, at least 1.5%, at least 2.0%, at least 2.5% or at least 3.0%. In further embodiments, $HbA_{1c}$ is reduced to less than 7.5%, less than 7.0%, less than 6.5%, less than 6.0%, less than 5.5%, less than 5.0%, less than 4.5% or less than 4.0%. In still another embodiment, average postprandial blood glucose levels do not exceed 175 mg/dl, 170 mg/dl, 165 mg/dl, 160 mg/dl, 155 mg/dl or 150 mg/dl. In another embodiment, overall average daily blood glucose concentration is less than 175 mg/dl, less than 165 mg/dl, less than 160 mg/dl, less than 155 mg/dl, less than 150 mg/dl, less than 145 mg/dl, less than 140 mg/dl, less than 135 mg/dl, less than 130 mg/dl, less than 125 mg/dl, less than 120 mg/dl, less than 110 mg/dl or less than 100 mg/dl.

The pharmaceutical compositions useful in the methods disclosed herein can be administered by any appropriate means known in the art, for example, intravenously, transmucosally, intranasally, orally, intramuscularly, subcutaneously, transdermally, by inhalation or by pulmonary administration. In one embodiment, the formulation is a sustained release or long acting formulation, that is, the formulation releases the at least one exendin, exendin agonist, or exendin analog agonist into the body over a given period of time, for example about 1 day, about 1 week or about 1 month. In further embodiments, the formulation is administered once a day, every other day, once a week, every other week, every third week, once a month, every other month, or every third month. In additional embodiments, the formulation further comprises a biocompatible polymer and sugar, for example sucrose. In one particular embodiment, the formulation is a long-acting formulation containing 5% (w/w) of at least one exendin, exendin agonist or exendin analog agonist, which is administered once a week at a dose equivalent to about from 3 µg/kg to about less than 100 µg/kg BID. In another particular embodiment, the formulation long-acting formulation containing 5% (w/w) of at least one exendin, exendin agonist or exendin analog agonist, is administered once a week at a dose equivalent to from about 10 µg/kg to about 30 µg/kg BID. In another particular embodiment, the formulation long-acting formulation containing 5% (w/w) of at least one exendin, exendin agonist or exendin analog agonist, is administered once a week at a dose equivalent to from about 3 µg/kg to about 30 µg/kg BID.

Further provided herein is the use of a pharmaceutical composition comprising an amount of at least one exendin, exendin agonist or exendin analog agonist sufficient to mediate the effects or treat the diseases or disorders as disclosed herein. Also provided is the use of at least one exendin, exendin agonist or exendin agonist analog to manufacture a medicament to mediate the effects or treat the diseases or disorders as disclosed herein.

DESCRIPTION OF THE INVENTION

Figure 1:
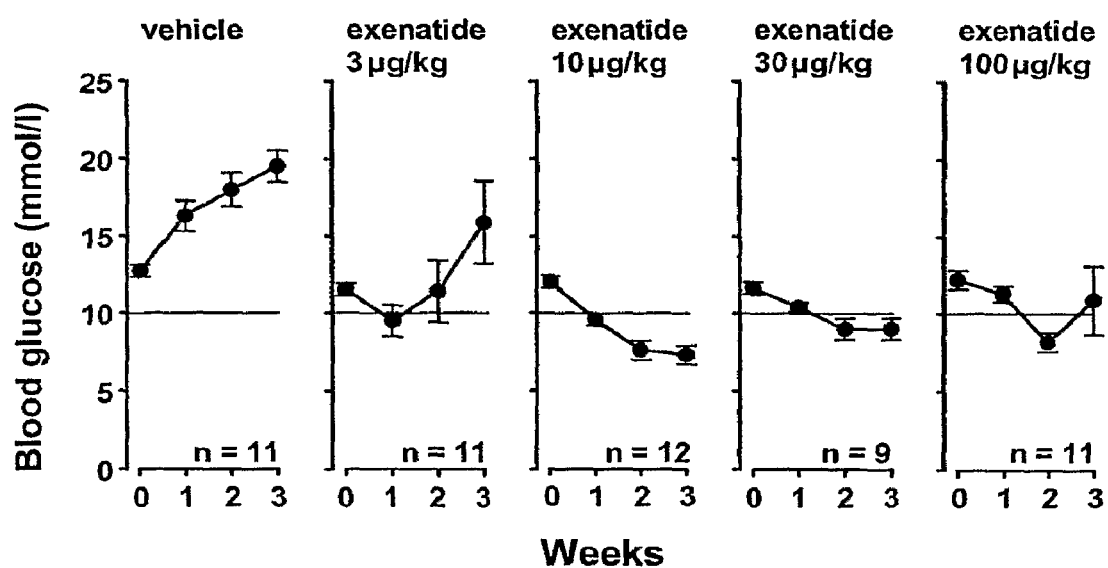
FIG. 1 depicts the correction of hyperglycemia after diabetes onset in NOD mice using exenatide at various doses.
Figure 2:
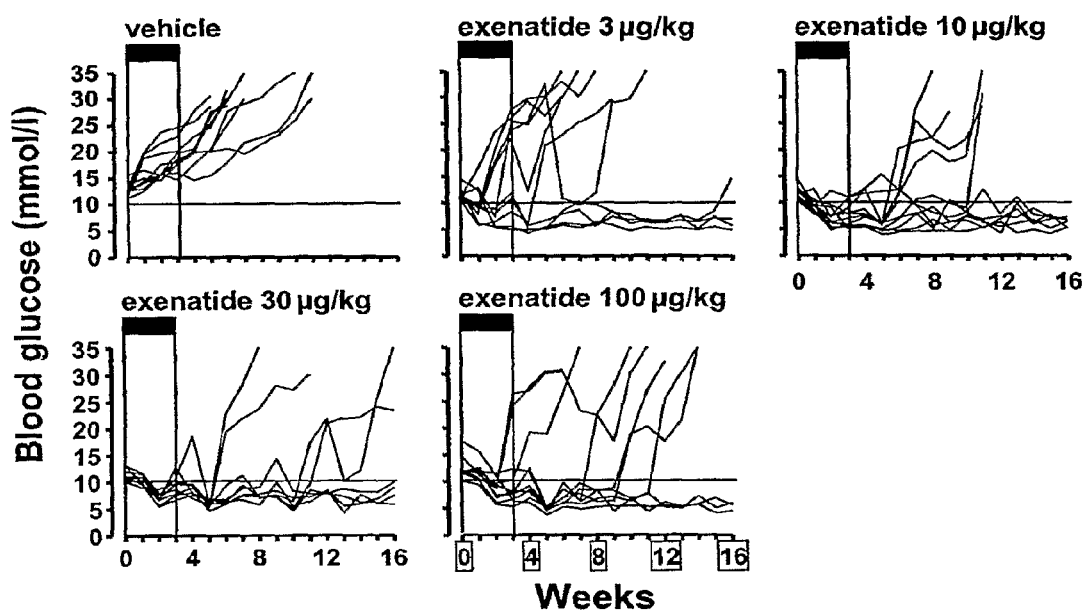
FIG. 2 depicts the delay in hyperglycemia progression and the restoration of normoglycemia after diabetes onset in NOD mice following a short course of exenatide.
Figure 3:
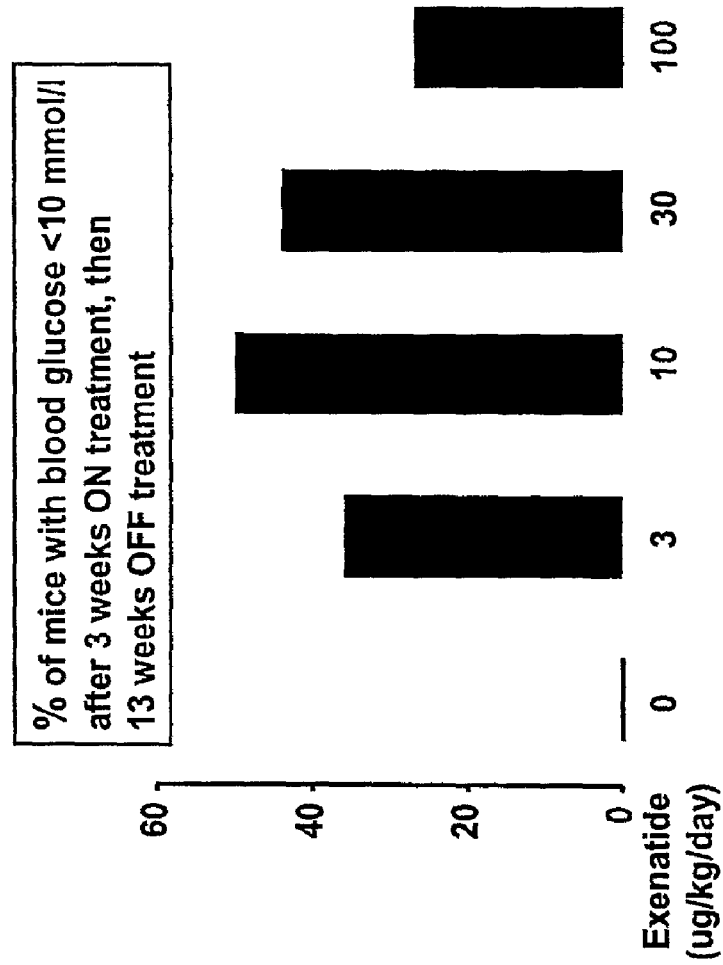
FIG. 3 shows the reversal of diabetes in NOD mice after exenatide administration is long lasting.
Figure 4:
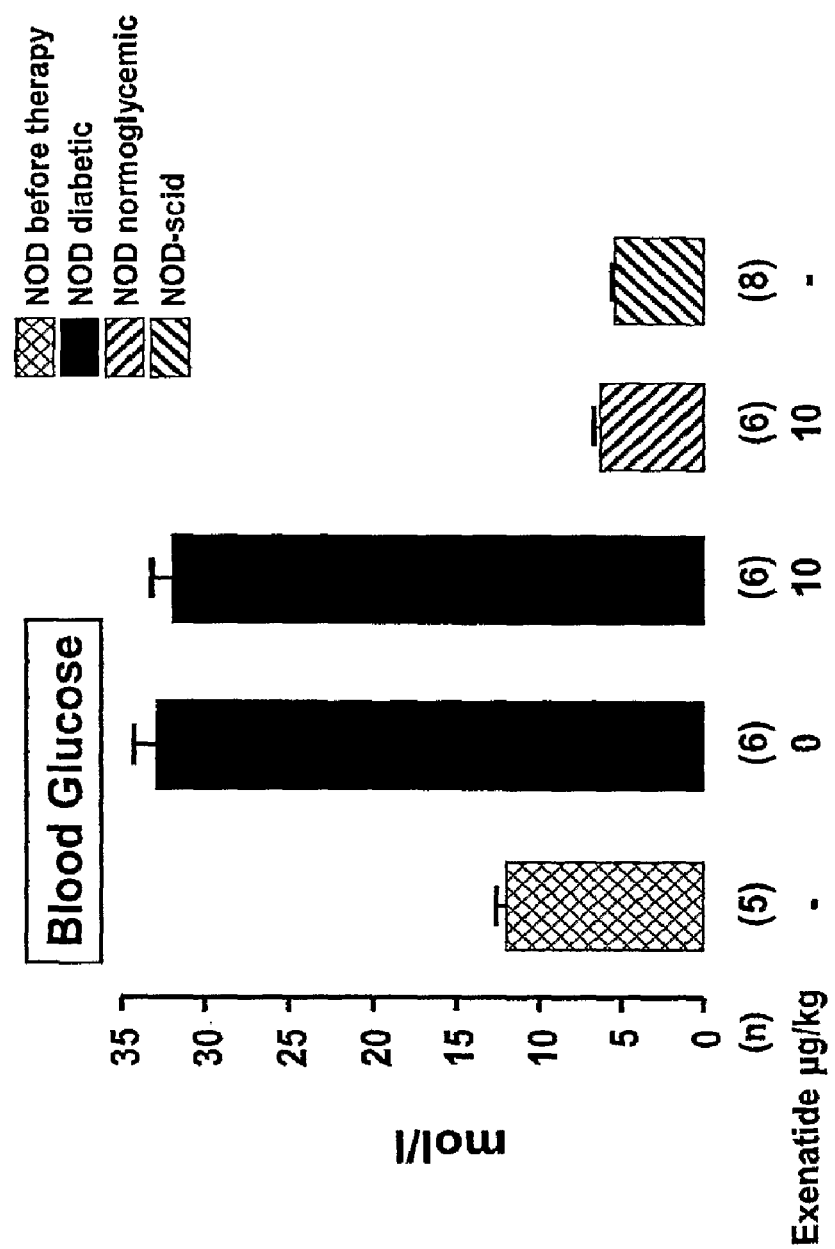
FIG. 4 illustrates a short course of exenatide results in long-term lower blood glucose in 50% of the exenatide-treated NOD mice.
Figure 5:
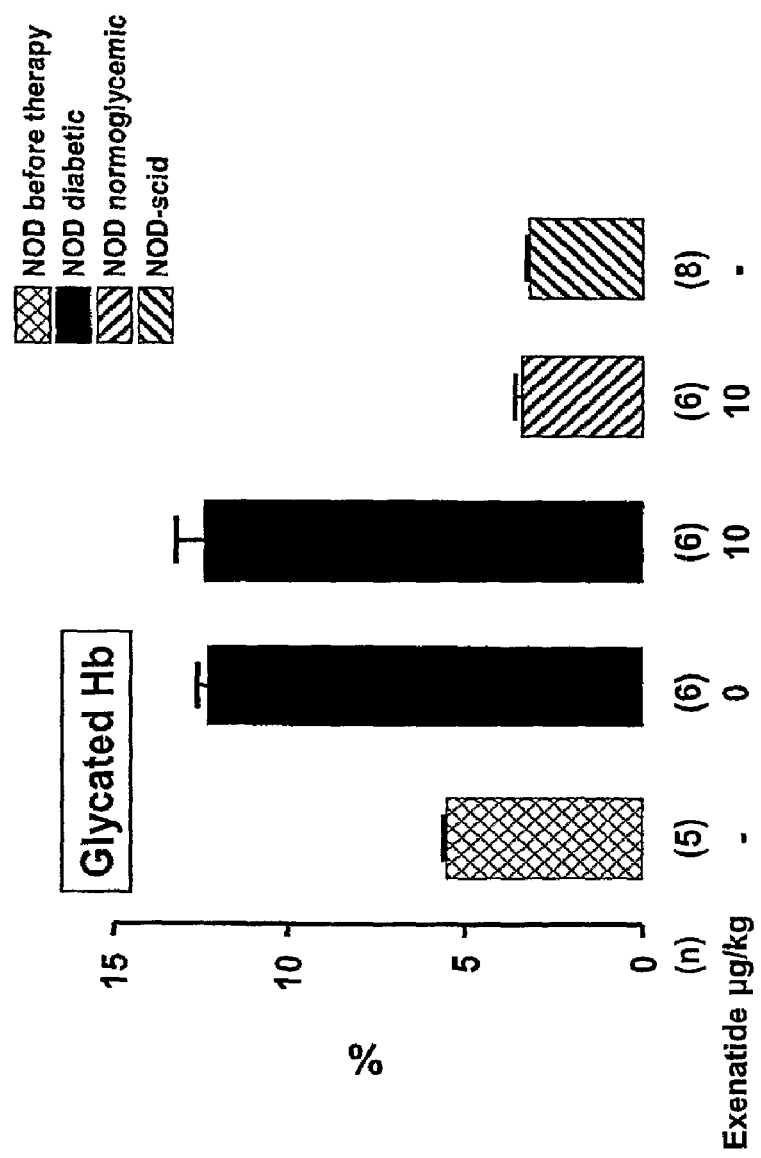
FIG. 5 depicts a short course of exenatide results long-term normalization of glycated Hb levels in 50% of the exenatide-treated NOD mice.
Figure 6:
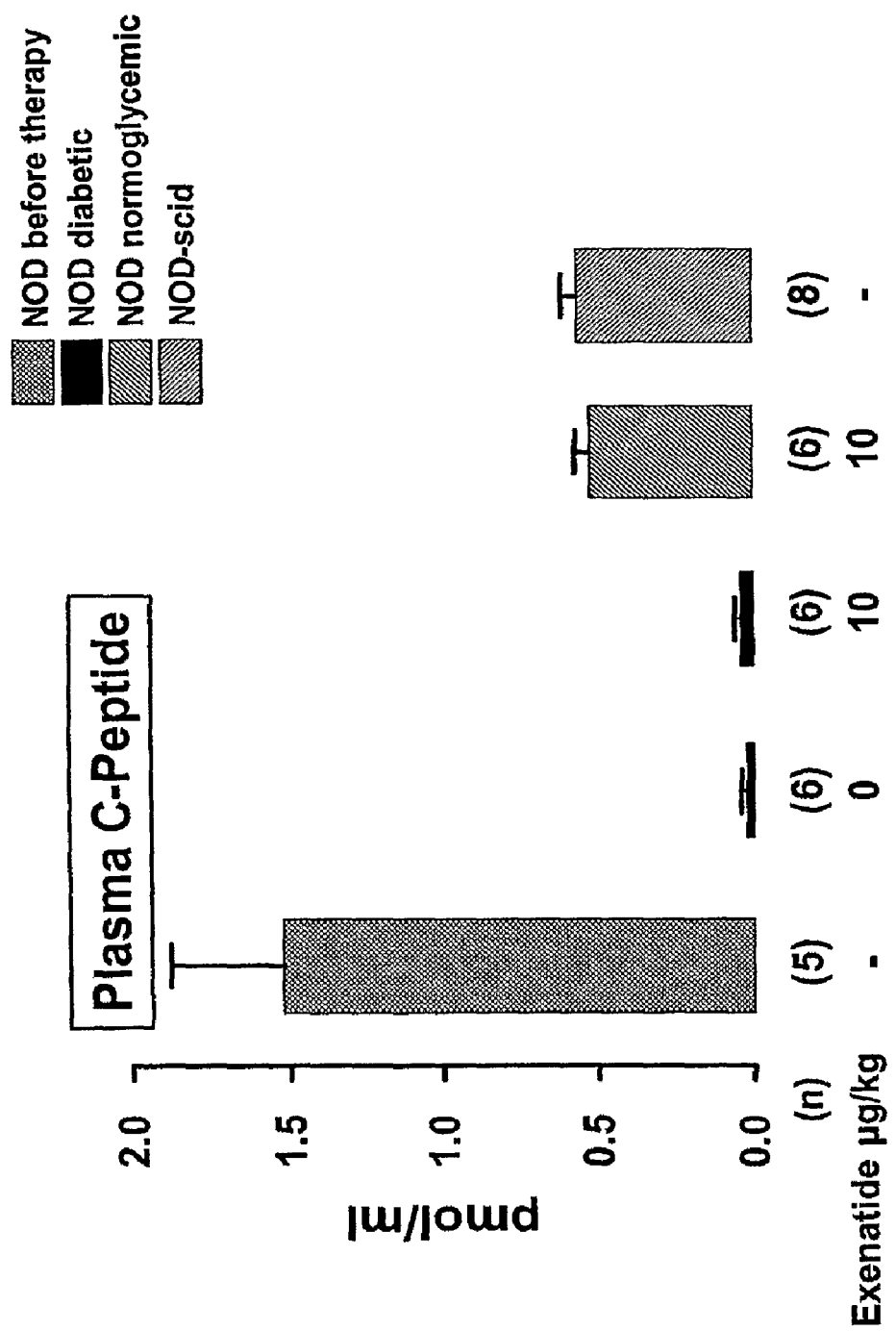
FIG. 6 shows a short course of exenatide results in long-term increases in plasma C-peptide levels in 50% of the exenatide-treated NOD mice.
Figure 7:
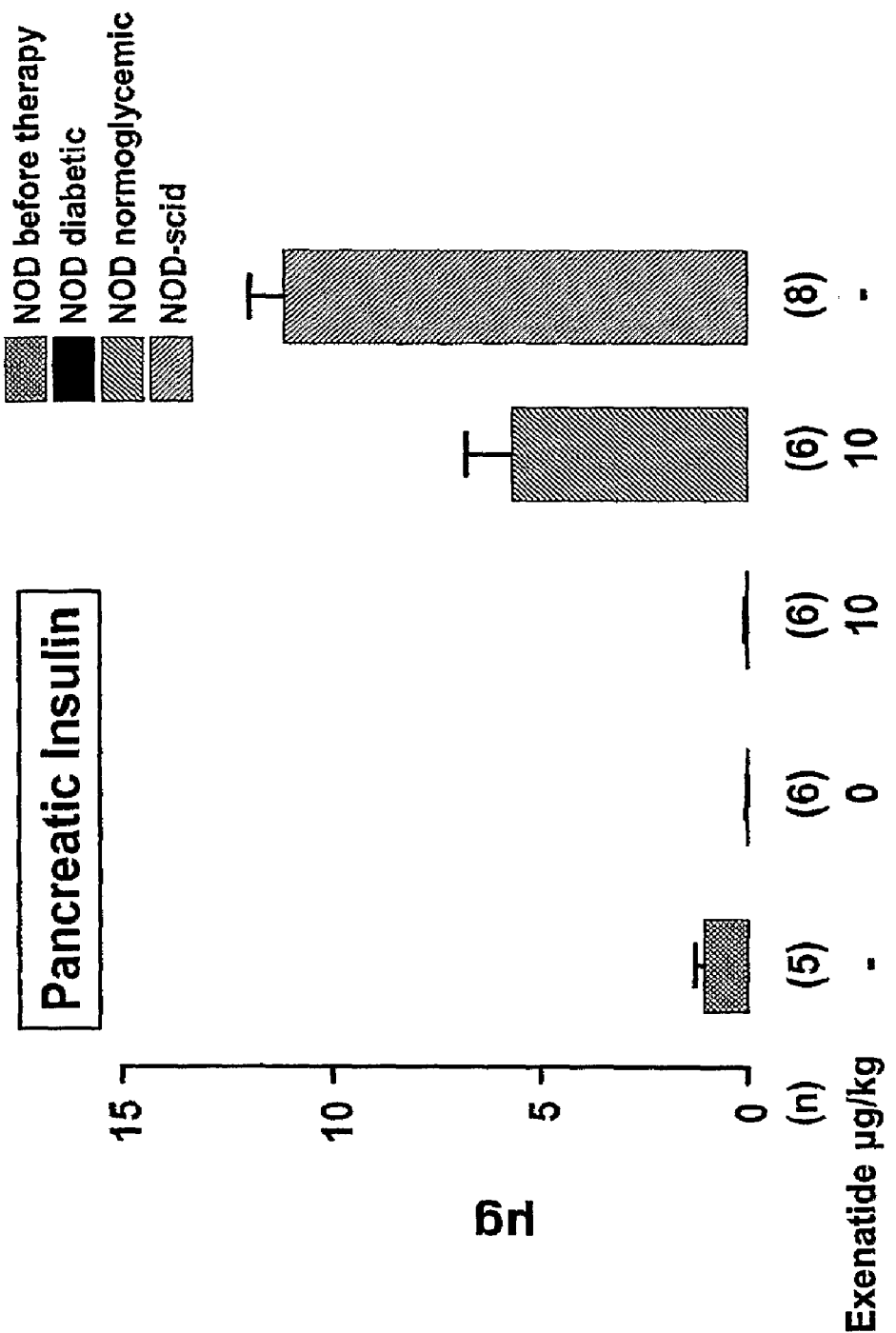
FIG. 7 shows sustained, increased pancreatic insulin levels in 50% of exenatide-treated NOD mice following a short course of exenatide treatment.
Figure 8:
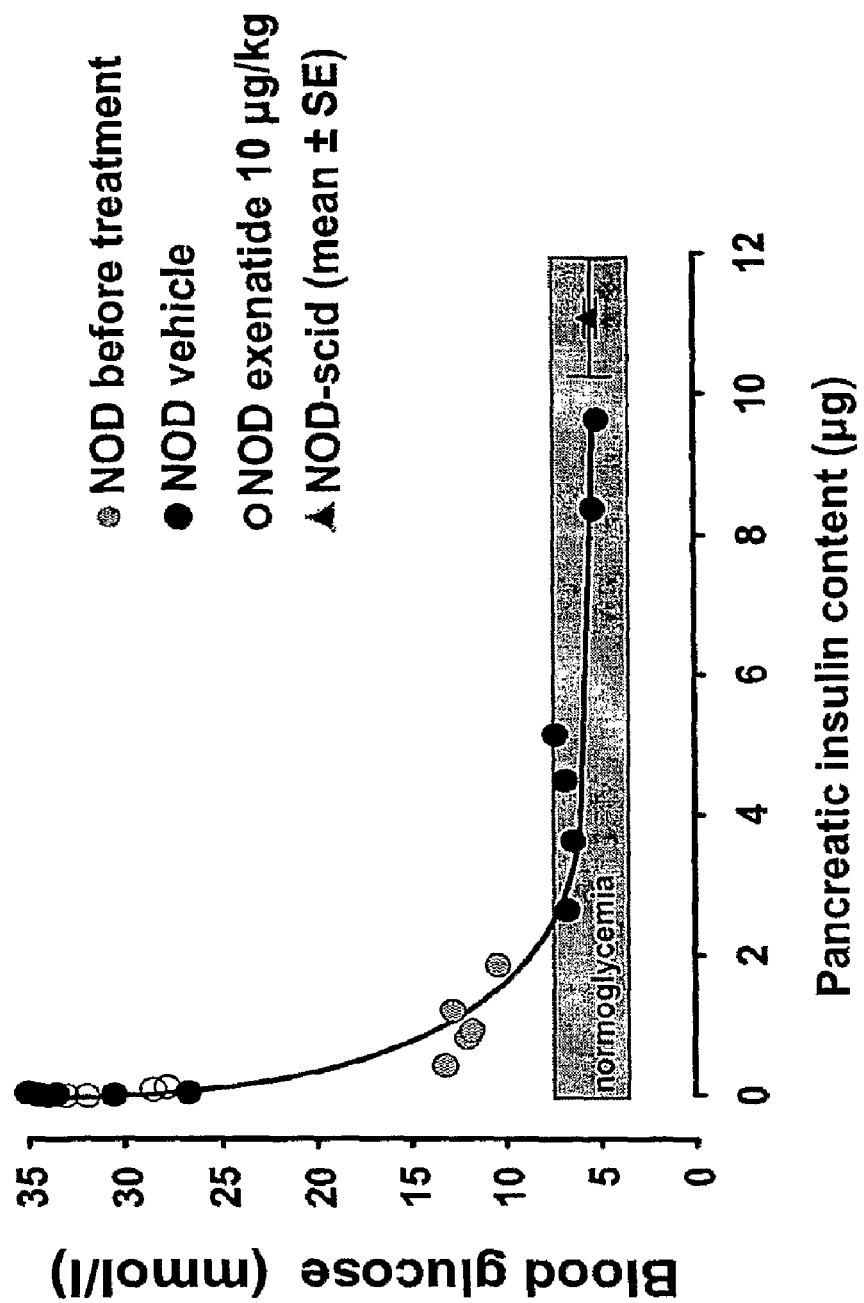
FIG. 8 shows a partial restoration of pancreatic insulin content corrects hyperglycemia in NOD mice.

Pancreatic β cell mass can increase in adult life in response to physiological stimuli such as pregnancy and obesity as well as regenerate following injury. Suarez-Pinzon et al., *Diabetes* 54:2596-601 (2005). Some studies suggest that β-cell regenerative processes can occur after diabetes onset in animal models for diabetes. For example, the autoimmune destruction and resulting diabetes in the non-obese diabetic (NOD) mouse is an animal model of human type I diabetes. In NOD mice, abrogation of the autoimmune response or transplantation of cells from diabetes-resistant donors results in a restoration of normoglycemia in NOD mice. See, e.g., Maki et al., *Proc. Nat'l Acad. Sci. USA* 89:3434-38 (1992); Kodama et al., *Science* 302:1223-27 (2003). Provided here are methods of achieving normoglycemia following diabetes onset by stimulating pancreatic β cell regeneration using an abbreviated course of exendin or exendin agonist analog, without requiring an abrogation of the anti-β cell autoimmune response through immunosuppressive therapies.

Provided herein are methods for inducing pancreatic β cell regeneration comprising administering to a subject in need thereof, a pharmaceutical composition comprising an exendin or an exendin agonist analog in an amount effective to restore normoglycemia, wherein said exendin or exendin agonist analog is administered over a short duration and said effective amount is from about 3 µg/kg to less than about 100 µg/kg BID. In one embodiment, the subject has early onset type I diabetes. In one embodiment, the subject has type I diabetes. In some embodiments the effective amount is from about 3 µg/kg to about 30 µg/kg BID. In further embodiments the effective amount is from about 10 µg/kg to about 30 µg/kg BID. In still further embodiments the effective amount is about 10 µg/kg BID.

Pancreatic β cell regeneration can be determined by any useful method. For example, β cell regeneration can be determined by analyzing C-peptide levels, Hb1Ac levels, as well as endogenous insulin production in patients not receiving insulin replacement therapy.

Further provided herein are methods to achieve a sustained delay in the progression of, or an amelioration of diabetes in a subject, or a delay in diabetes onset in a subject at risk for diabetes, comprising an abbreviated course of administration of a pharmaceutical composition comprising an exendin or an exendin agonist analog in an amount effective to induce β cell regeneration. In one embodiment, the subject has type I diabetes. In some embodiments, the delay in diabetes progression or the amelioration of diabetes occurs in the absence of immunosuppressive therapy. In one embodiment, the effective amount is about 3 µg/kg to less than about 100 µg/kg administered twice a day. In some embodiments the effective amount is from about 10 µg/kg to about 30 µg/kg administered twice a day. In some embodiments the effective amount is from about 3 µg/kg to about 30 µg/kg administered twice a day. In some embodiments the effective amount is about 10 µg/kg BID.

As used herein, the term "an abbreviated course of administration" includes administration over a limited time period. In some embodiments, the pharmaceutical compositions disclosed herein are administered once or twice daily for at least one week, at least two weeks, at least three weeks, at least 4 weeks, at least 5 weeks or at least 6 weeks. In other embodiments, the pharmaceutical composition disclosed herein is administered weekly for at least at least one week, at least two weeks, at least three weeks, at least 4 weeks, at least 5 weeks, or at least 6 weeks. In still other embodiments, the pharmaceutical composition disclosed herein is administered monthly for at least one month, at least two month, at least three months, at least 4 months, at least 5 months, or at least 6 months. It is contemplated that once a patient has returned to normoglycemia, the detection of one or more indicator that diabetic state may be returning (e.g., detection of hyperglycemia, increased Hb1Ac levels, increased thrist and urination, decreased C-peptide), subsequent abbreviated administration of the exendin or exendin agonist analog may be employed.

Characteristics of type I diabetes include hyperglycemia, increased thirst and urine production, increased cholesterol in the blood, and increased blood triglyceride concentration. In some embodiments, the absence or improvement of one or more of these characteristics can also indicate a delay in diabetes progression or amelioration of diabetes. For example, a decrease in thrist and urine production, a decrease in cholesterol in the blood, a reduction in postprandial glycemia, a reduction in fasting blood glucose levels, or a decrease in blood triglyceride concentration can be indicators of a delay in diabetes progression or amelioration of diabetes.

In determining the length of the abbreviated course of administration, in some embodiments, the exendin, exendin agonist or exendin analog agonist can be administered according to the methods disclosed herein for a period sufficient to achieve a target $HbA_{1c}$, a target fasting glucose level, a target C peptide concentration, a target overall daily blood glucose concentration, etc. In one embodiment, the exendin, exendin agonist or exendin analog agonist is administered according to methods disclosed herein for a period sufficient to lower or stabilize fasting glucose levels, reducing or eliminating high or higher than desired fasting glucose levels.

In some embodiments, the ameriolation of diabetes (e.g., achieving normoglycemia) after the cessation of exendin or exendin agonist analog treatment is for at least 1 week, at least 2 weeks, at least 3 weeks, at least 1 month, at least 2 months, at least 3 months, at least 4 months, at least 5 months, at least 6 months, or at least 1 year.

In some embodiments, the sustained delay in the progression of diabetes is for at least 1 month, at least 2 months, at least 3 months, at least 4 months, at least 5 months, at least 6 months, at least 1 year, at least 18 months, or at least 2 years.

The terms "$HbA_{1c}$", "$A_{1c}$", "glycated hemoglobin" or "glycohemoglobin" refer to glycosylated hemoglobin.

In other embodiments, $HbA_{1c}$ is reduced by at least 0.5%, at least 1.0%, at least 1.5%, at least 2.0%, at least 2.5% or at least 3.0%. In further embodiments, $HbA_{1c}$ is reduced to less than 7.5%, less than 7.0%, less than 6.5%, less than 6.0%, less than 5.5%, less than 5.0%, less than 4.5% or less than 4.0%. In still another embodiment, average postprandial blood glucose levels do not exceed 175 mg/dl, 170 mg/dl, 165 mg/dl, 160 mg/dl, 155 mg/dl or 150 mg/dl. In another embodiment, overall average daily blood glucose concentration is less than 175 mg/dl, less than 165 mg/dl, less than 160 mg/dl, less than 155 mg/dl, less than 150 mg/dl, less than 145 mg/dl, less than 140 mg/dl, less than 135 mg/dl, less than 130 mg/dl, less than 125 mg/dl, less than 120 mg/dl, less than 110 mg/dl or less than 100 mg/dl.

The pharmaceutical compositions useful in the methods disclosed herein can be administered by any appropriate means known in the art, for example, intravenously, transmucosally, intranasally, orally, intramuscularly, subcutaneously, transdermally, by inhalation or by pulmonary administration. In one embodiment, the formulation is a sustained release or long acting formulation, that is, the formulation releases the at least one exendin, exendin agonist, or exendin analog agonist into the body over a given period of time, for example about 1 day, about 1 week or about 1 month. See, e.g., U.S. Provisional Appl. No. 60/709,604, filed 19 Aug. 2005; U.S. Provisional Appl. No. 60/779,216, filed 3 Mar. 2006. In further embodiments, the formulation is administered once a day, every other day, once a week, every other week, every third week, once a month, every other month, or every third month. In additional embodiments, the formulation further comprises a biocompatible polymer and sugar, for example sucrose. In one particular embodiment, the formulation is a long-acting formulation containing a drug load of at least one exendin, exendin agonist or exendin analog agonist to achieve a dose equivalent to from about 3 µg/kg to less than about 100 µg/kg BID, from about 3 µg/kg to about 30 µg/kg BID, from about 10 µg/kg to about 30 µg/kg BID, or about 10 µg/kg BID when administered once a week at a dose of 2.0 mg.

In another particular embodiment, the formulation long-acting formulation containing drug load of at least one exendin, exendin agonist or exendin analog agonist to achieve the equivalent of from about 10 µg/kg to about 30 µg/kg BID, from about 3 µg/kg to about 30 µg/kg BID, from about 10 µg/kg to about 30 µg/kg BID, or about 10 µg/kg BID when administered once a week at a dose of 0.8 mg.

In one embodiment, the exendin, exendin agonist or exendin analog agonist is administered in an extended release, slow release, sustained release or long acting formulation. In one embodiment, the exendin or exendin agonist is administered in a polymer-based sustained release formulation. Such polymer-based sustained release formulations are described, for example, in U.S. patent application Ser. No. 11/107,550, filed Apr. 15, 2005.

The exendin, exendin agonist or exendin analog agonist can be administered by any useful method available. In one embodiment, the exendin or exendin agonist is administered subcutaneously.

In some embodiments, the exendin is exendin-4. In some embodiments, the exendin agonist analog is a peptide compound of Formula I, Formula II, Formula III, Formula IV, Formula V, Formula VI or Formula VII.

The term "exendin" includes naturally occurring exendin peptides that are found in the salivary secretions of the Gila monster. Exendins of particular interest include exendin-3 [SEQ ID NO:2], which is present in the salivary secretions of *Heloderma horridum*, and exendin-4 [SEQ ID NO:1], a 39 amino acid peptide which is naturally present in the salivary secretions of *Heloderma suspectrum* (Eng, J., et al., *J. Biol. Chem.*, 265:20259-62, 1990; Eng., J., et al., *J. Biol. Chem.*, 267:7402-05, 1992). Animal testing of exendin-4 has shown that its ability to lower blood glucose persists for several hours. Exendin-4, as it occurs in the salivary secretions of the Gila monster, is an amidated peptide. It should be appreciated, however, that the exendins, exendin agonists and exendin analog agonists for use in the methods described herein are not limited to the amidated forms, but include that acid form or any other physiologically active form of the molecule, including pharmaceutically acceptable salts.

Exendin-4 was first thought to be a component of the venom. It now appears that exendin-4 is devoid of toxicity, and that it instead is made in salivary glands in the Gila monster. The exendins have some sequence similarity to several members of the glucagon-like peptide family, with the highest identity, 53%, being to GLP-1[7-36]$NH_2$ (Goke, et al., *J. Biol. Chem.*, 268:19650-55, 1993).

Exendin "agonist activity" as used herein means having the biological activity of an exendin, but it is understood that the activity of the activity can be either less potent or more potent than the native exendin. Other exendin agonists include, e.g., chemical compounds specifically designed to active that receptor or receptors at which an exendin exerts its effect on pancreatic β cell regeneration.

The term "insulin resistance" as used herein, describes a subnormal biological response to a given concentration of insulin (i.e., decreased glucose transport across the cell membrane in response to insulin).

The terms "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all such solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions.

Certain exendin sequences are compared to the sequence of GLP-1 in Table 1.

TABLE 1 a. HAEGTFTSDVSSYLEGQAAKEFIAWLVKGR(NH
b. HSDGTFTSDLSKQMEEEAVRLFIEWLKNGGPSSGAPPPS (NH$_2$)
c. DLSKQMEEEAVRLFIEWLKNGGPSSGAPPPS (NH$_2$)
d. HGEGTFTSDLSKQMEEEAVRLFIEWLKNGGPSSGAPPPS (NH$_2$)
e. HSDATFTAEYSKLLAKLALQKYLESILGSSTSPRPPSS
f. HSDATFTAEYSKLLAKLALQKYLESILGSSTSPRPPS
g. HSDAIFTEEYSKLLAKLALQKYLASILGSRTSPPP (NH$_2$)
h. HSDAIFTQQYSKLLAKLALQKYLASILGSRTSPPP (NH$_2$)

a = GLP-1(7-36) (NH$_2$) [SEQ ID NO: 3].
b = exendin 3 (NH$_2$) [SEQ ID NO: 2].
c = exendin 4 (9-39)(NH$_2$) [SEQ ID NO: 4].
d = exendin 4 (NH$_2$) [SEQ ID NO: 1].
e = helospectin I [SEQ ID NO: 5].
f = helospectin II [SEQ ID NO: 6].
g = helodermin (NH$_2$) [SEQ ID NO: 7].
h = Q$^8$, Q$^9$ helodermin (NH$_2$) [SEQ ID NO: 8].

As used in this specification, by "exendin agonist" is meant a compound which elicits a biological activity of a exendin reference peptide, preferably having a potency better than the exendin reference peptide, or within five orders of magnitude (plus or minus) of potency compared to the exendin reference peptide, for example, 4, 3, 2, or 1 order of magnitude, when evaluated by art-known measures such as receptor binding/competition studies. In one embodiment, the term refers to a compound which elicits a biological effect similar to that of the exendin reference peptide, for example a compound (1) having activity in glucose lowering and/or pancreatic β regeneration assays similar to the exendin reference peptide, and (2) which optionally binds specifically in a reference receptor assay or in a competitive binding assay with labeled exendin reference peptide. Preferably, the agonists will bind in such assays with an affinity of less than 1 μM, and more preferably with an affinity of less than 1-5 nM. Such agonists may comprise a polypeptide comprising an active fragment of a reference peptide or a small chemical molecule. In one embodiment, the exendin agonist is a peptide. In another embodiment, exendin agonists do not include GLP-1 and variants, analogs and derivatives thereof.

Exendin analog agonists include exendin analogs with agonist activity in which one or more naturally occurring amino acids are inserted, eliminated or replaced with another amino acid(s). Exendin analogs are peptide analogs of exendin-4.

Exendin analogs include peptides that are encoded by polynucleotides that express biologically active exendin analogs with agonist activity, as defined herein. Exendin analogs may be peptides containing one or more amino acid substitutions, additions or deletions, compared with reference exendin, for example, exendin-4. In one embodiment, the number of substitutions, deletions, or additions is 30 amino acids or less, 25 amino acids or less, 20 amino acids or less, 15 amino acids or less, 10 amino acids or less, 5 amino acids or less or any integer between 30 and 1, inclusive. In one aspect, the substitutions include one or more conservative substitutions. A "conservative" substitution denotes the replacement of an amino acid residue by another, biologically active, similar residue. Examples of conservative substitutions include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

TABLE 2

| ORIGINAL RESIDUE | EXEMPLARY SUBSTITUTIONS |
| --- | --- |
| ALA | SER, THR |
| ARG | LYS |
| ASN | HIS, SER |
| ASP | GLU, ASN |
| CYS | SER |
| GLN | ASN, HIS |
| GLU | ASP |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that exendin analogs include the peptides described herein which have been chemically derivatized or altered, for example, peptides with non-natural amino acid residues (e.g., taurine, β- and γ-amino acid residues and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid.

Such derivativatized peptides include exendins, exendin agonists and exendin analog agonists conjugated to one or more water soluble polymer molecules, such as polyethylene glycol ("PEG") or albumin, or gelatin, or fatty acid chains of various lengths (e.g., stearyl, palmitoyl, octanoyl, etc.), or by the addition of polyamino acids, such as poly-his, poly-arg, poly-lys, and poly-ala. Modifications to the exendins, exendin agonists and exendin analog agonists can also include small molecule substituents, such as short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the polypeptides. Alternatively, there may be multiple sites of derivatization along the hybrid polypeptide. Substitution of one or more amino acids with lysine, aspartic acid, glutamic acid, or cysteine may provide additional sites for derivatization. See, e.g., U.S. Pat. Nos. 5,824,784 and 5,824,778. In one embodiment, the polypeptides may be conjugated to one, two, or three polymer molecules.

The water-soluble polymer molecules are typically linked to an amino, carboxyl, or thiol group, and may be linked by N or C terminus, or at the side chains of lysine, aspartic acid, glutamic acid, or cysteine. Alternatively, the water-soluble polymer molecules may be linked with diamine and dicarboxylic groups. In one embodiment, the polypeptides are conjugated to one, two, or three PEG molecules through an epsilon amino group on a lysine amino acid.

Also included in the present invention are exendin analog sequences having greater than 50% sequence identity, greater than 60% sequence identity, greater than 70% sequence identity, greater than 80% sequence identity, greater than 90% sequence identity, greater than 95% sequence identity, greater than 99% sequence identity or any percent identity between 50% and 99%, to a reference exendin peptide, for example, (1) SEQ ID NOS: 1 and 2; and (2) to truncated sequences thereof, wherein said truncated sequences contain at least 10 amino acids, at least 20 amino acids, at least 25 amino acids, at least 30 amino acids, at least 35 amino acids, at least 38 amino acids or N−1 amino acids where N equals the number of amino acids in the full length or reference peptide or protein. As used herein, sequence identity refers to a comparison made between two molecules using standard algorithms well known in the art. The preferred algorithm for calculating sequence identity for the present invention is the Smith-Waterman algorithm, where an exendin, for example SEQ ID NO: 1 [i.e. exendin-4], is used as the reference sequence to define the percentage identity of a comparison peptide over its length. The choice of parameter values for matches, mismatches, and insertions or deletions is arbitrary, although some parameter values have been found to yield more biologically realistic results than others. One preferred set of parameter values for the Smith-Waterman algorithm is set forth in the "maximum similarity segments" approach, which uses values of 1 for a matched residue and −⅓ for a mismatched residue (a residue being either a single nucleotide or single amino acid). Waterman, *Bull. Math. Biol.* 46; 473 (1984). Insertions and deletions (indels), x, are weighted as $x_k=1+\frac{1}{3}k$, where k is the number of residues in a given insert or deletion. Id.

Novel exendin analogs with agonist activity include those described in commonly owned PCT Application Serial No. PCT/US98/16387 filed Aug. 6, 1998, entitled "Novel Exendin Agonist Compounds," which claims the benefit of U.S. Patent Application Ser. No. 60/055,404, filed Aug. 8, 1997, both of which are herein incorporated by reference.

Other novel exendin analogs with agonist activity include those described in commonly owned PCT Application Serial No. PCT/US98/24210, filed Nov. 13, 1998, entitled "Novel Exendin Agonist Compounds," which claims the benefit of U.S. Provisional Application No. 60/065,442 filed Nov. 14, 1997, both of which are herein incorporated by reference.

Still other novel exendin analogs with agonist activity include those described in commonly owned PCT Application Serial No. PCT/US98/24273, filed Nov. 13, 1998, entitled "Novel Exendin Agonist Compounds," which claims the benefit of U.S. Provisional Application No. 60/066,029 filed Nov. 14, 1997, both of which are herein incorporated by reference.

Still other exendin analogs with agonist activity include those described in commonly owned PCT Application Serial No. PCT/US97/14199, filed Aug. 8, 1997, entitled "Methods for Regulating Gastrointestinal Activity," which is a continuation-in-part of U.S. patent application Ser. No. 08/694,954 filed Aug. 8, 1996, both of which are hereby incorporated by reference.

Still other exendin analogs with agonist activity include those described in commonly owned PCT Application Serial No. PCT/US98/00449, filed Jan. 7, 1998, entitled "Use of Exendins and Agonists Thereof for the Reduction of Food Intake," which claims priority to U.S. Provisional Application No. 60/034,90 filed Jan. 7, 1997, both of which are hereby incorporated by reference.

Still other exendin analogs with agonist activity include those described in commonly owned PCT Application Serial No. PCT/US01/00719, filed Jan. 9, 2001, entitled "Use of Exendins and Agonists Thereof for Modulation of Triglyceride Levels and Treatment of Dyslipidemia," which claims priority to U.S. Provisional Application No. 60/175,365 filed Jan. 10, 2000, both of which are hereby incorporated by reference.

Still other exendin analogs with agonist activity include those described in commonly owned PCT Application Serial No. PCT/US00/00902, filed Jan. 14, 2000, entitled "Novel Exendin Agonist Formulations and Methods of Administration Thereof," which claims priority to U.S. Provisional Application No. 60/116,380 filed Jan. 14, 1999, both of which are hereby incorporated by reference.

Still other exendin analogs with agonist activity include those described in commonly owned PCT Application Serial No. PCT/US03/16699, filed May 28, 2003, entitled "Novel Exendin Agonist Formulations and Methods of Administration Thereof," which claims priority to U.S. application Ser. No. 10/157,224 filed May 28, 2002, both of which are hereby incorporated by reference.

Still other exendin analogs with agonist activity include those described in commonly owned PCT Application Serial No. PCT/US00/00942, filed Jan. 14, 2000, entitled "Methods of Glucagon Suppression," which claims priority to U.S. Provisional Application No. 60/132,017 filed Apr. 30, 1999, both of which are hereby incorporated by reference.

Still other exendin analogs with agonist activity include those described in commonly owned PCT Application Serial No. PCT/US00/14231, filed May 23, 2000, entitled "Use of Exendins and Agonists Thereof for the Treatment of Gestational Diabetes Mellitus," which claims priority to U.S. application Ser. No. 09/323,867 filed Jun. 1, 1999, both of which are hereby incorporated by reference.

Still other exendin analogs with agonist activity include those described in commonly owned PCT Application Serial No. PCT/US99/02554, filed Feb. 5, 1999, entitled "Inotropic and Diuretic Effects of Exendin and GLP-1," which claims priority to U.S. Provisional Application No. 60/075,122 filed Feb. 13, 1998, both of which are hereby incorporated by reference.

Still other exendin analogs with agonist activity include those described in commonly owned PCT Application Serial No. PCT/US05/04178 filed Feb. 11, 2005, entitled "Hybrid Polypeptides with Selectable Properties".

Activity as exendin agonists and exendin analogs with agonist activity can be indicated, for example, by activity in the assays described herein. Effects of exendins or exendin agonists on pancreatic β cell regeneration can be identified, evaluated, or screened for, using the methods described herein, or other art-known or equivalent methods for determining effect on pancreatic β cell regeneration or function.

Certain exemplary exendin analogs with agonist activity include: exendin-4 (1-30) [SEQ ID NO:9: His Gly Glu Gly Thr Phe Thr Ser Asp Leu Ser Lys Gln Met Glu Glu Glu Ala Val Arg Leu Phe Ee Glu Trp Leu Lys Asn Gly Gly]; exendin-4 (1-30) amide [SEQ ID NO:10: His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$]; exendin-4 (1-28) amide [SEQ ID NO: 11: His Gly Glu Gly Thr Phe Thr Ser Asp Leu Ser Lys Gln Met Glu Glu Glu Ala Val Arg Leu Phe Ile Glu Trp Leu Lys Asn-NH$_2$]; $^{14}$Leu, $^{25}$Phe exendin-4 amide [SEQ ID NO:12: His Gly Gly Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$]; $^{14}$Lu, $^{25}$Phe exendin-4 (1-28) amide [SEQ ID NO:13: His Gly Glu Gly Thr Phe Thr Ser Asp Leu Ser Lys Gln Leu Glu Glu Glu Ala Val Arg Leu Phe Ile Glu Phe Leu Lys Asn-NH$_2$]; and $^{14}$Leu, $^{22}$Ala, $^{25}$Phe exendin-4 (1-28) amide [SEQ ID NO: 14: His Gly Glu Gly Thr Phe Thr Ser Asp Leu Ser Lys Gln Leu Glu Glu Glu Ala Val Arg Leu Ala Ile Glu Phe Leu Lys Asn-NH$_2$].

Also included within the scope of the methods provided herein are pharmaceutically acceptable salts of the compounds of formulae I-VIII and pharmaceutical compositions including said compounds and salts thereof.

Formula I

Exendin analogs with agonist activity also include those described in U.S. Provisional Application No. 60/065,442, including compounds of the formula (I) [SEQ ID NO:15]:

Xaa$_1$ Xaa$_2$ Xaa$_3$ Gly Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$;

wherein

Xaa$_1$ is His, Arg or Tyr;
Xaa$_2$ is Ser, Gly, Ala or Thr;
Xaa$_3$ is Ala, Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{18}$ is Ala or Val;
Xaa$_{20}$ is Ala or Arg;
Xaa$_{21}$ is Ala or Leu;
Xaa$_{22}$ is Ala, Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
Z$_1$ is —OH,
—NH$_2$
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$ or
Gly Gly Xaa$_{31}$ Ser Ser Gly Ala Xaa$_{36}$ Xaa$_{37}$ Xaa$_{38}$-Z$_2$;

Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; and Z$_2$ is —OH or —NH$_2$;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala.

Exemplary N-alkyl groups for N-alkylglycine, N-alkylpentylglycine and N-alkylalanine include lower alkyl groups preferably of 1 to about 6 carbon atoms, more preferably of 1 to 4 carbon atoms.

Exemplary exendin analogs include those wherein Xaa$_1$ is His or Tyr. In one embodiment, Xaa$_1$ is His.

Provided are those compounds wherein Xaa$_2$ is Gly.

Provided are those compounds wherein Xaa$_{14}$ is Leu, pentylglycine or Met.

Exemplary compounds are those wherein Xaa$_{25}$ is Trp or Phe.

Exemplary compounds are those where Xaa$_6$ is Phe or naphthylalanine; Xaa$_{22}$ is Phe or naphthylalanine and Xaa$_{23}$ is Ile or Val.

Provided are compounds wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.
Preferably Z$_2$ is —NH$_2$.

According to one embodiment, provided are compounds of formula (I) wherein Xaa$_1$ is His or Tyr, more preferably His; Xaa$_2$ is Gly; Xaa$_6$ is Phe or naphthylalanine; Xaa$_{14}$ is Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine. More preferably Z$_1$ is —NH$_2$.

According to one embodiment, exemplary compounds include those of formula (I) wherein: Xaa$_1$ is His or Arg; Xaa$_2$ is Gly or Ala; Xaa$_3$ is Asp or Glu; Xaa$_5$ is Ala or Thr; Xaa$_6$ is Ala, Phe or nephthylalaine; Xaa$_7$ is Thr or Ser; Xaa$_8$ is Ala, Ser or Thr; Xaa$_9$ is Asp or Glu; Xaa$_{10}$ is Ala, Leu or pentylglycine; Xaa$_{11}$ is Ala or Ser; Xaa$_{12}$ is Ala or Lys; Xaa$_{13}$ is Ala or Gln; Xaa$_{14}$ is Ala, Leu or pentylglycine; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Phe or naphthylalanine; Xaa$_{23}$ is He, Val or tert-butylglycine; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$, Gly Gly Xaa$_{31}$ Ser Ser-Z$_2$, Gly Gly Xaa$_{31}$ Ser Ser Gly-Z$_2$, Gly Gly Xaa$_{31}$ Ser Ser Gly Ala-Z$_2$, Gly Gly Xaa$_{31}$ Ser Ser Gly Ala Xaa$_{36}$-Z$_2$, Gly Gly Xaa$_{31}$ Ser Ser Gly Ala Xaa$_{36}$ Xaa$_{37}$-Z$_2$, Gly Gly Xaa$_{31}$ Ser Ser Gly Ala Xaa$_{36}$ Xaa$_{37}$ Xaa$_{38}$-Z$_2$; Xaa$_{31}$, Xaa$_{36}$, Xaa$_{37}$ and Xaa$_{38}$ being independently Pro homoproline, thioproline or N-methylalanine; and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala. Especially preferred compounds include those set forth in PCT application Serial No. PCT/US98/24210, filed Nov. 13, 1998, entitled "Novel Exendin Agonist Compounds" identified therein as compounds 2-23.

According to another embodiment, provided are compounds where Xaa$_{14}$ is Leu, Ile, Val or pentylglycine, more preferably Leu or pentylglycine, and Xaa$_{25}$ is Phe, Tyr or naphthylalanine, more preferably Phe or naphthylalanine. These compounds will be less susceptive to oxidative degration, both in vitro and in vivo, as well as during synthesis of the compound.

Formula II

Exendin analogs with agonist activity also include those described in U.S. Provisional Application No. 60/066,029, including compounds of the formula (II)[SEQ ID NO:16]:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;
wherein:
$Xaa_1$ is His, Arg, Tyr, Ala, Norval, Val or Norleu;
$Xaa_2$ is Ser, Gly, Ala or Thr;
$Xaa_3$ is Ala, Asp or Glu;
$Xaa_4$ is Ala, Norval, Val, Norleu or Gly;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Ala, Norval, Val, Norleu, Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,
 —$NH_2$,
 Gly-$Z_2$,
 Gly Gly-$Z_2$,
 Gly Gly $Xaa_{31}$-$Z_2$,
 Gly Gly $Xaa_{31}$ Ser-$Z_2$,
 Gly Gly $Xaa_{31}$ Ser Ser-$Z_2$,
 Gly Gly $Xaa_{31}$ Ser Ser Gly-$Z_2$,
 Gly Gly $Xaa_{31}$ Ser Ser Gly Ala-$Z_2$,
 Gly Gly $Xaa_{31}$ Ser Ser Gly Ala $Xaa_{36}$-$Z_2$,
 Gly Gly $Xaa_{31}$ Ser Ser Gly Ala $Xaa_{36}$ $Xaa_{37}$-$Z_2$,
 Gly Gly $Xaa_{31}$ Ser Ser Gly Ala $Xaa_{36}$ $Xaa_{37}$ $Xaa_{38}$-$Z_2$ or
 Gly Gly $Xaa_{31}$ Ser Ser Gly Ala $Xaa_{36}$ $Xaa_{37}$ $Xaa_{38}$ $Xaa_{39}$-$Z_2$;
$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;
$Xaa_{39}$ is Ser or Tyr; and
$Z_2$ is —OH or —$NH_2$;
provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{18}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Exemplary N-alkyl groups for N-alkylglycine, N-alkylpentylglycine and N-alkylalanine include lower alkyl groups preferably of 1 to about 6 carbon atoms, more preferably of 1 to 4 carbon atoms. Suitable compounds of formula (II) include those described in application Serial No. PCT/US98/24273, filed Nov. 13, 1998, entitled "Novel Exendin Agonist Compounds."

In one embodiment, such exendin analogs include those wherein $Xaa_1$ is His, Ala or Norval. More preferably $Xaa_1$ is His or Ala. Most preferably $Xaa_1$ is His.

Provided are those compounds of formula (II) wherein $Xaa_2$ is Gly.

Provided are those compounds of formula (II) wherein $Xaa_3$ is Ala.

Provided are those compounds of formula (II) wherein $Xaa_4$ is Ala.

Provided are those compounds of formula (II) wherein $Xaa_9$ is Ala.

Provided are those compounds of formula (II) wherein $Xaa_{14}$ is Leu, pentylglycine or Met.

Exemplary compounds of formula (II) are those wherein $Xaa_{25}$ is Trp or Phe.

Exemplary compounds of formula (II) are those where $Xaa_6$ is Ala, Phe or naphthylalanine; $Xaa_{22}$ is Phe or naphthylalanine; and $Xaa_{23}$ is Ile or Val.

Provided are compounds of formula (II) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one embodiment, provided are compounds of formula (II) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —$NH_2$.

According to another embodiment, exemplary compounds include those of formula (II) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Compounds of formula (II) include those described in application Serial No. PCT/US98/24273, filed Nov. 13, 1998, entitled "Novel Exendin Agonist Compounds" as having the amino acid sequence of SEQ ID NOS:5-93 therein.

According to still another embodiment, provided are compounds of formula (II) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula III

Also useful within the scope of the present invention are narrower genera of compounds having peptides of various lengths, for example genera of compounds which do not include peptides having a length of 28, 29 or 30 amino acid residues, respectively. Additionally, the present invention includes narrower genera of compounds described in PCT Application Serial No. PCT/US98/24210, filed Nov. 13, 1998, entitled "Novel Exendin Agonist Compounds" and having particular amino acid sequences, for example, compounds of the formula (I) [SEQ ID NO:17]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein:
$Xaa_1$ is His or Arg;
$Xaa_2$ is Gly or Ala;
$Xaa_3$ is Ala, Asp or Glu;
$Xaa_5$ is Ala or Thr;
$Xaa_6$ is Ala, Phe or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu or pentylglycine;
$Xaa_{11}$ is Ala or Ser;
$Xaa_{12}$ is Ala or Lys;
$Xaa_{13}$ is Ala or Gln;
$Xaa_{14}$ is Ala, Leu or pentylglycine;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe or naphthylalanine;
$Xaa_{23}$ is Ile, Val or tert-butylglycine;
$Xaa_{24}$ is Ala, Glu or Asp;
$Xaa_{25}$ is Ala, Trp, or Phe;
$Xaa_{26}$ is Ala or Leu;
$Xaa_{27}$ is Ala or Lys;
$Xaa_{28}$ is Ala or Asn;
$Z_1$ is —OH,
—$NH_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Glly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$ or
Gly Gly $Xaa_{31}$ Ser Ser Gly Ala $Xaa_{36}$ $Xaa_{37}$ $Xaa_{38}$-$Z_2$;
$Xaa_{31}$, $Xaa_{36}$, $Xaa_{37}$ and $Xaa_{38}$ are independently selected from the group consisting of Pro, homoproline, thioproline and N-methylylalanine; and
$Z_2$ is —OH or —$NH_2$;
provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and pharmaceutically acceptable salts thereof.

Formula IV

Additionally, the present invention includes narrower genera of peptide compounds described in PCT Application Serial No. PCT/US98/24273, filed Nov. 13, 1998, entitled "Novel Exendin Agonist Compounds" as having particular amino acid sequences, for example, compounds of the formula [IV] [SEQ ID NO:18]:

$Xaa_1$ $Xaa_2$ $Xaa_3$ $Xaa_5$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein:
$Xaa_1$ is His or Ala;
$Xaa_2$ is Gly or Ala;
$Xaa_3$ is Ala, Asp or Glu;
$Xaa_4$ is Ala or Gly;
$Xaa_5$ is Ala or Thr;
$Xaa_6$ is Ala, Phe or naphthylalanine;
$Xaa_7$ is Thr or Ser;
$Xaa_8$ is Ala, Ser or Thr;
$Xaa_9$ is Ala, Asp or Glu;
$Xaa_{10}$ is Ala, Leu or pentylglycine;
$Xaa_{11}$ is Ala or Ser;
$Xaa_{12}$ is Ala or Lys;
$Xaa_{13}$ is Ala or Gln;
$Xaa_{14}$ is Ala, Leu, Met or pentylglycine;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe or naphthylalanine;
$Xaa_{23}$ is Ile, Val or tert-butylglycine;
$Xaa_{24}$ is Ala, Glu or Asp;
$Xaa_{25}$ is Ala, Trp or Phe;
$Xaa_{26}$ is Ala or Leu;
$Xaa_{27}$ is Ala or Lys;
$Xaa_{28}$ is Ala or Asn;
$Z_1$ is —OH,
—$NH_2$,
Gly-$Z_2$,
Gly Gly-$Z_2$
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$
Gly Gly $Xaa_{31}$ Ser Ser Gly Ala $Xaa_{36}$ $Xaa_{37}$ $Xaa_{38}$-$Z_2$
Gly Gly $Xaa_{31}$ Ser Ser Gly Ala $Xaa_{36}$ $Xaa_{37}$ $Xaa_{38}$ Ser-$Z_2$;
$Xaa_{31}$, $Xaa_{36}$, $Xaa_{37}$ and $Xaa_{38}$ are independently Pro, homoproline, thioproline, or N-methylylalanine; and
$Z_2$ is —OH or —$NH_2$;
provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$, and $Xaa_{28}$ are Ala; and provided that, if $Xaa_1$ is His, Arg or Tyr, then at least one of $Xaa_3$, $Xaa_4$ and $Xaa_9$ is Ala; and pharmaceutically acceptable salts thereof.

Exemplary compounds of formula (IV) include those wherein $Xaa_1$ is His or Ala. Preferably, $Xaa_1$ is His.

Exemplary compounds of formula (IV) include those wherein $Xaa_2$ is Gly.

Exemplary compounds of formula (IV) include those wherein $Xaa_4$ is Ala.

Exemplary compounds of formula (IV) include those wherein $Xaa_9$ is Ala.

Exemplary compounds of formula (IV) include those wherein $Xaa_{14}$ is Leu, pentylglycine or Met.

Exemplary compounds of formula (IV) include those wherein $Xaa_{25}$ is Trp or Phe.

Exemplary compounds of formula (IV) include those wherein $Xaa_6$ is Ala, Phe or naphthylalanine; $Xaa_{22}$ is Phe or naphthylalanine; and $Xaa_{23}$ is Ile or Val.

Exemplary compounds of formula (IV) include those wherein $Z_1$ is —NH$_2$.

Exemplary compounds of formula (IV) include those wherein Xaa$_{31}$, Xaa$_{36}$, Xaa$_{37}$ and Xaa$_{38}$ are independently selected from the group consisting of Pro, homoproline, thioproline and N-alkylalanine.

Exemplary compounds of formula (IV) include those wherein $Z_2$ is —NH$_2$.

Exemplary compounds of formula (IV) include those wherein $Z_1$ is —NH$_2$.

Formula V

Also provided are compounds described in PCT application PCT/US98/24210, filed Nov. 13, 1998, entitled "Novel Exendin Agonist Compounds", including compounds of the formula (V) [SEQ ID NO:19]:

Xaa$_1$ Xaa$_2$ Xaa$_3$ Gly Xaa$_5$ Xaa$_6$ Xaa$_7$ Xaa$_8$ Xaa$_9$ Xaa$_{10}$
Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$
Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$;

wherein
Xaa$_1$ is His, Arg or Tyr or 4-imidazopropionyl;
Xaa$_2$ is Ser, Gly, Ala or Thr;
Xaa$_3$ is Ala, Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala, Leu or Lys-NH$^\epsilon$—R where R is Lys, Arg, C$_1$-C$_{10}$ straight chain or branched alkanoyl or cycloalkylalkanoyl;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Lys, Asn, Ala or Lys-NH$^\epsilon$—R where R is Lys, Arg, C$_1$-C$_{10}$ straight chain or branched alkanoyl or cycloalkylalkanoyl;
X$_{28}$ is Lys, Asn, Ala or Lys-NH$^\epsilon$—R where R is Lys, Arg, C$_1$-C$_{10}$ straight chain or branched alkanoyl or cycloalkylalkanoyl;
Z$_1$ is —OH,
—NH$_2$,
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$ or
Gly Gly Xaa$_{31}$ Ser Ser Gly Ala Xaa$_{36}$ Xaa$_{37}$ Xaa$_{38}$-Z$_2$;
Xaa$_{31}$, Xaa$_{36}$, Xaa$_{37}$ and Xaa$_{38}$ are independently selected from the group consisting of Pro, homoproline, 3Hyp, 4Hyp, thioproline, N-alkylglycine, N-alkylpentylglycine and N-alkylalanine; and
Z$_2$ is —OH or —NH$_2$;

provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, and Xaa$_{26}$ are Ala. Also within the scope of the methods provided herein are pharmaceutically acceptable salts of the compound of formula (V) and pharmaceutical compositions including said compounds and salts thereof.

Exemplary exendin analogs of formula (V) include those wherein Xaa$_1$ is His, Tyr or 4-imidazopropionyl. More preferably Xaa$_1$ is His.

Provided are those compounds of formula (V) wherein Xaa$_1$ is 4-imidazopropionyl.

Provided are those compounds of formula (V) wherein Xaa$_2$ is Gly.

Exemplary compounds of formula (V) are those wherein Xaa$_{14}$ is Leu, pentylglycine or Met.

Exemplary compounds of formula (V) are those wherein Xaa$_{25}$ is Trp or Phe.

According to one embodiment, provided are compounds of formula (V) wherein Xaa$_6$ is Phe or naphthylalanine; and Xaa$_{22}$ is Phe or naphthylalanine; and Xaa$_{23}$ is Ile or Val. More preferably, Z$_1$ is —NH$_2$. According to one embodiment, provided are compounds of formula (V) wherein Xaa$_{31}$, Xaa$_{36}$, Xaa$_{37}$ and Xaa$_{38}$ are independently selected from the group consisting of Pro, homoproline, thioproline and N-alkylalanine. Preferably, Z$_2$ is —NH$_2$.

Exemplary compounds of formula (V) include those wherein X$_{27}$ is Lys or Lys-NH$^\epsilon$R where R is Lys, Arg, C$_1$-C$_{10}$ straight chain or branched alkanoyl and Xaa$_{28}$ is Asn or Ala. Preferred compounds of formula (V) include compounds described in PCT application Serial No. PCT/US98/24210, filed Nov. 13, 1998, entitled "Novel Exendin Agonist Compounds" and identified therein as Compound Nos. 62-69.

Provided exendin analogs include those wherein Xaa$_1$ is His.

Provided are those compounds of formula (V) wherein Xaa$_2$ is Gly.

Provided are those compounds of formula (V) wherein Xaa$_3$ is Ala.

Provided are those compounds of formula (V) wherein Xaa$_{14}$ is Leu, pentylglycine or Met.

Provided compounds of formula (V) are those wherein Xaa$_{25}$ is Trp or Phe.

Exemplary compounds of formula (V) are those where Xaa$_6$ is Ala, Phe or naphthylalanine; Xaa$_{22}$ is Phe or naphthylalanine; and Xaa$_{23}$ is Ile or Val.

Provided are compounds of formula (V) wherein Xaa$_{31}$, Xaa$_{36}$, Xaa$_{37}$ and Xaa$_{38}$ are independently selected from Pro, homoproline, thioproline and N-alkylalanine.

Preferably Z$_1$ is —NH$_2$.

Preferably Z$_2$ is —NH$_2$.

According to one embodiment, provided are compounds of formula (V) wherein Xaa$_1$ is His or Tyr, more preferably His; Xaa$_2$ is Ala or Gly; Xaa$_6$ is Phe or naphthylalanine; Xaa$_{14}$ is Ala, Leu, pentylglycine or Met; Xaa$_{22}$ is Phe or naphthylalanine; Xaa$_{23}$ is Ile or Val; Xaa$_{31}$, Xaa$_{36}$, Xaa$_{37}$ and Xaa$_{38}$ are independently selected from Pro, homoproline, thioproline or N-alkylalanine; and Xaa$_{39}$ is Ser or Tyr, more preferably Ser. More preferably Z$_1$ is —NH$_2$.

According to one embodiment, provided compounds include those of formula (V) wherein: Xaa$_1$ is His; Xaa$_2$ is Gly or Ala; Xaa$_3$ is Ala, Asp or Glu; Xaa$_4$ is Gly; Xaa$_5$ is Ala or Thr; Xaa$_6$ is Phe or naphthylalanine; Xaa$_7$ is Thr or Ser; Xaa$_8$ is Ala, Ser or Thr; Xaa$_9$ is Asp or Glu; Xaa$_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$ and $Xaa_4$ is Ala. Compounds of formula (V) include those described in PCT application Serial No. PCT/US98/24210, filed Nov. 13, 1998, entitled "Novel Exendin Agonist Compounds" and having the amino acid sequences identified therein as SEQ ID NOS:5-93.

According to one embodiment, provided are compounds of formula (V) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula VI

Also provided are peptide compounds described in PCT Application Serial No. PCT/US98/24273, filed Nov. 13, 1998, entitled "Novel Exendin Agonist Compounds", including compounds of the formula (VI) [SEQ ID NO:20]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$
$Xaa_{11}$ $Xaa_{12}$ $Xaa_{13}$ $Xaa_{14}$ $Xaa_{15}$ $Xaa_{16}$ $Xaa_{17}$ Ala $Xaa_{19}$ $Xaa_{20}$
$Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;
wherein $Xaa_1$ is His, Arg, Tyr, Ala, Norval, Val, Norleu or 4-imidazopropionyl;

$Xaa_2$ is Ser, Gly, Ala or Thr;

$Xaa_3$ is Ala, Asp or Glu;

$Xaa_4$ is Ala, Norval, Val, Norleu or Gly;

$Xaa_5$ is Ala or Thr;

$Xaa_6$ is Ala, Phe, Tyr or naphthylalanine;

$Xaa_7$ is Thr or Ser;

$Xaa_8$ is Ala, Ser or Thr;

$Xaa_9$ is Ala, Norval, Val, Norleu, Asp or Glu;

$Xaa_{10}$ is Ala, Leu, Ile, Val, pentylglycine or Met;

$Xaa_{11}$ is Ala or Ser;

$Xaa_{12}$ is Ala or Lys;

$Xaa_{13}$ is Ala or Gln;

$Xaa_{14}$ is Ala, Leu, Ile, pentylglycine, Val or Met;

$Xaa_{15}$ is Ala or Glu;

$Xaa_{16}$ is Ala or Glu;

$Xaa_{17}$ is Ala or Glu;

$Xaa_{19}$ is Ala or Val;

$Xaa_{20}$ is Ala or Arg;

$Xaa_{21}$ is Ala, Leu or Lys-NH$^\epsilon$—R where R is Lys, Arg, $C_{1-10}$ straight chain or branched alkanoyl or cycloalleyl-alkanoyl;

$Xaa_{22}$ is Phe, Tyr or naphthylalanine;

$Xaa_{23}$ is Ile, Val, Leu, pentylglycine, tert-butylglycine or Met;

$Xaa_{24}$ is Ala, Glu or Asp;

$Xaa_{25}$ is Ala, Trp, Phe, Tyr or naphthylalanine;

$Xaa_{26}$ is Ala or Leu;

$Xaa_{27}$ is Lys, Asn, Lys-NH$^\epsilon$—R or Ala where R is Lys, Arg, $C_1$-$C_{10}$ straight chain or branched alkanoyl or cycloalkylalkanoyl;

$Xaa_{28}$ is Lys, Asn, Lys-NH$^\epsilon$—R or Ala where R is Lys, Arg, $C_1$-$C_{10}$ straight chain or branched alkanoyl or cycloalkylalkanoyl;

$Z_1$ is —OH,
—NH$_2$,
Gly-$Z_2$,
Gly Gly-$Z_2$,
Gly Gly $Xaa_{31}$-$Z_2$,
Gly Gly $Xaa_{31}$ Ser-$Z_2$,
Gly Gly $Xaa_{31}$ Ser Ser-$Z_2$,
Gly Gly $Xaa_{31}$ Ser Ser Gly-$Z_2$,
Gly Gly $Xaa_{31}$ Ser Ser Gly Ala-$Z_2$,
Gly Gly $Xaa_{31}$ Ser Ser Gly Ala $Xaa_{36}$-$Z_2$,
Gly Gly $Xaa_{31}$ Ser Ser Gly Ala $Xaa_{36}$ $Xaa_{37}$-$Z_2$,
Gly Gly $Xaa_{31}$ Ser Ser Gly Ala $Xaa_{36}$ $Xaa_{37}$ $Xaa_{38}$-$Z_2$ or
Gly Gly $Xaa_{31}$ Ser Ser Gly Ala $Xaa_{36}$ $Xaa_{37}$ $Xaa_{38}$ $Xaa_{39}$-$Z_2$;

$Xaa_{31}$, $Xaa_{36}$, $Xaa_{37}$ and $Xaa_{38}$ are independently selected from the group consisting of Pro, homoproline, 3Hyp, 4Hyp, thioproline, N-alkylglycine, N-alkylpentylglycine and N-alkylalanine;

$Xaa_{39}$ is Ser or Tyr; and $Z_2$ is —OH or —NH$_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, are Ala; and provided also that, if $Xaa_1$ is His, Arg, Tyr, or 4-imidazopropionyl then at least one of $Xaa_3$, $Xaa_4$ and $Xaa_9$ is Ala.

Exemplary compounds of formula (VI) include those wherein $Xaa_1$ is His, Ala, Norval or 4-imidazopropionyl. Preferably, $Xaa_1$ is His, or 4-imidazopropionyl or Ala, more preferably His or 4-imidazopropionyl.

Exemplary compounds of formula (VI) include those wherein $Xaa_2$ is Gly.

Exemplary compounds of formula (VI) include those wherein $Xaa_4$ is Ala.

Exemplary compounds of formula (VI) include those wherein $Xaa_9$ is Ala.

Exemplary compounds of formula (VI) include those wherein $Xaa_{14}$ is Leu, pentylglycine or Met.

Exemplary compounds of formula (VI) include those wherein $Xaa_{25}$ is Trp or Phe.

Exemplary compounds of formula (VI) include those wherein $Xaa_6$ is Ala, Phe or naphthylalanine; $Xaa_{22}$ is Phe or naphthylalanine; and $Xaa_{23}$ is Ile or Val.

Exemplary compounds of formula (VI) include those wherein $Z_1$ is —NH$_2$.

Exemplary compounds of formula (VI) include those wherein $Xaa_{31}$, $Xaa_{36}$, $Xaa_{37}$ and $Xaa_{38}$ are independently selected from the group consisting of Pro, homoproline, thioproline and N-alkylalanine.

Exemplary compounds of formula (VI) include those wherein $Xaa_{39}$ is Ser.

Exemplary compounds of formula (VI) include those wherein $Z_2$ is —NH$_2$.

Exemplary compounds of formula (VI) include those 42 wherein $Z_1$ is —NH$_2$.

Exemplary compounds of formula (VI) include those wherein $Xaa_{21}$ is Lys-NH$^\epsilon$—R where R is Lys, Arg, $C_1$-$C_{10}$ straight chain or branched alkanoyl.

Exemplary compounds of formula (VI) include those wherein $X_{27}$ is Lys or Lys-NH$^\epsilon$—R, where R is Lys, Arg, $C_1$-$C_{10}$ straight chain or branched alkanoyl and $X_{28}$ is Asn or Ala.

Other compounds of formula (VI) include those described in PCT Application Serial No. PCT/US98/24273, filed Nov. 13, 1998, entitled "Novel Exendin Agonist Compounds" as having an amino acid sequence selected from those identified therein as SEQ ID NOS:95-110.

Formula VII

Compounds useful in the methods provided herein are exendin analogs with agonist activity described in U.S. patent application Ser. No. 09/003,869, filed Jan. 7, 1998, entitled "Use of Exendins And Agonists Thereof For The Reduction of Food Intake", including compounds of the formula (VII) [SEQ ID NO:21]:

$Xaa_1$ $Xaa_2$ $Xaa_3$ Gly Thr $Xaa_6$ $Xaa_7$ $Xaa_8$ $Xaa_9$ $Xaa_{10}$
Ser Lys Gln $Xaa_{14}$ Glu Glu Glu Ala Val Arg Leu
$Xaa_{22}$ $Xaa_{23}$ $Xaa_{24}$ $Xaa_{25}$ Leu Lys Asn Gly Gly $Xaa_{31}$
Ser Ser Gly Ala $Xaa_{36}$ $Xaa_{37}$ $Xaa_{38}$ $Xaa_{39}$-Z wherein:

$Xaa_1$ is His, Arg or Tyr;
$Xaa_2$ is Ser, Gly, Ala or Thr;
$Xaa_3$ is Asp or Glu;
$Xaa_6$ is Phe, Tyr or naphthalanine;
$Xaa_7$ is Thr or Ser; $Xaa_8$ is Ser or Thr;
$Xaa_9$ is Asp or Glu;
$Xaa_{10}$ is Leu, Ile, Val, pentylglycine or Met;
$Xaa_{14}$ is Leu, Ile, pentylglycine, Val or Met;
$Xaa_{22}$ is Phe, Tyr or naphthalanine;
$Xaa_{23}$ is Ile, Val, Leu, pentylglycine, tert-butylglycine or Met;
$Xaa_{24}$ is Glu or Asp;
$Xaa_{25}$ is Trp, Phe, Tyr, or naphthylalanine;
$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;
$Xaa_{39}$ is Ser, Thr or Tyr; and Z is —OH or —NH$_2$;

with the proviso that the compound does not have the formula of either SEQ ID NOS:1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Also useful in the present invention are pharmaceutically acceptable salts of the compounds of formula (VII).

Exemplary exendin analogs include those wherein $Xaa_1$ is His or Tyr. More preferably $Xaa_1$ is His.

Provided are those compounds wherein $Xaa_2$ is Gly.

Provided are those compounds wherein $Xaa_{14}$ is Leu, pentylglycine or Met.

Exemplary compounds include those wherein $Xaa_{25}$ is Trp or Phe.

Also provided are compounds where $Xaa_6$ is Phe or naphthalanine; $Xaa_{23}$ is Ile or Val and $Xaa_{31}$, $Xaa_{36}$, $Xaa_{37}$ and $Xaa_{38}$ are independently selected from Pro, homoproline, thioproline or N-alkylalanine. Preferably N-alkylalanine has a N-alkyl group of 1 to about 6 carbon atoms.

According to one embodiment, $Xaa_{36}$, $Xaa_{37}$ and $Xaa_{38}$ are the same amino acid reside.

Provided are compounds wherein $Xaa_{39}$ is Ser or Tyr, more preferably Ser.

Preferably Z is —NH$_2$.

According to one embodiment, provided are compounds of formula (VII) wherein $Xaa_1$ is His or Tyr, preferably His; $Xaa_2$ is Gly; $Xaa_6$ is Phe or naphthalanine; $Xaa_{14}$ is Leu, pentylglycine or Met; $Xaa_{22}$ is Phe or naphthalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably Z is —NH$_2$.

According to another embodiment, exemplary compounds include those of formula (VII) wherein: $Xaa_1$ is His or Arg; $Xaa_2$ is Gly; $Xaa_3$ is Asp or Glu; $Xaa_6$ is Phe or naphthylalanine; $Xaa_7$ is Thr or Ser; $Xaa_8$ is Ser or Thr; $Xaa_9$ is Asp or Glu; $Xaa_{10}$ is Leu or pentylglycine; $Xaa_{14}$ is Leu or pentylglycine; $Xaa_{22}$ is Phe or naphthylalanine; $Xaa_{23}$ is Ile, Val or t-butyltylglycine; $Xaa_{24}$ is Glu or Asp; $Xaa_{25}$ is Trp or Phe; $Xaa_{31}$, $Xaa_{36}$, $Xaa_{37}$, and $Xaa_{38}$ are independently Pro, homoproline, thioproline, or N-methylalanine; $Xaa_{39}$ is Ser or Tyr: and Z is —OH or —NH$_2$; with the proviso that the compound does not have the formula of either SEQ ID NOS:1 or 2. More preferably Z is —NH$_2$.

According to another embodiment, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds are believed to exhibit advantageous duration of action and to be less subject to oxidative degration, both in vitro and in vivo, as well as during synthesis of the compound.

Formula VIII

Also provided are compounds described in PCT Application Serial No. PCT/US98/16387, filed Aug. 6, 1998, entitled "Novel Exendin Agonist Compounds", including compounds of the formula (VIII) [SEQ ID NO:22]:

$Xaa_1$ $Xaa_2$ $Xaa_3$ Gly Thr $Xaa_6$ $Xaa_7$ $Xaa_8$ $Xaa_9$ $Xaa_{10}$
Ser Lys Gln $Xaa_{14}$ Glu Glu Glu Ala Val Arg Leu
$Xaa_{22}$ $Xaa_{23}$ $Xaa_{24}$ $Xaa_{25}$ Leu $Xaa_{27}$ $Xaa_{28}$ Gly Gly $Xaa_{31}$
Ser Ser Gly Ala $Xaa_{36}$ $Xaa_{37}$ $Xaa_{38}$ $Xaa_{39}$-Z wherein:

$Xaa_1$ is His, Arg, Tyr or 4-imidazopropionyl;
$Xaa_2$ is Ser, Gly, Ala or Thr;
$Xaa_3$ is Asp or Glu;
$Xaa_6$ is Phe, Tyr or naphthalanine;
$Xaa_7$ is Thr or Ser;
$Xaa_8$ is Ser or Thr;
$Xaa_9$ is Asp or Glu;
$Xaa_{10}$ is Leu, Ile, Val, pentylglycine or Met;
$Xaa_{14}$ is Leu, Ile, pentylglycine, Val or Met;
$Xaa_{22}$ is Phe, Tyr or naphthylalanine;
$Xaa_{23}$ is Ile, Val, Leu, pentylglycine, tert-butylglycine or Met;
$Xaa_{24}$ is Glu or Asp;
$Xaa_{25}$ is Trp, Phe, Tyr, or naphthylalanine;
$Xaa_{27}$ is Lys, Asn, or Lys-NH$^\epsilon$—R where R is Lys, Arg, $C_1$-$C_{10}$ straight chain or branched alkanoyl or cycloalkylalkanoyl;
$Xaa_{28}$ is Lys, Asn, or Lys-NH$^\epsilon$—R where R is Lys, Arg, $C_1$-$C_{10}$ straight chain or branched alkanoyl or cycloalkylalkanoyl;
$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;
$Xaa_{39}$ is Ser, Thr or Tyr; and
Z is —OH or —NH$_2$;
with the proviso that the compound does not have the formula of either SEQ ID NOS:7 or 9. Suitable compounds of formula (VIII) include compounds described in PCT Application Serial No. PCT/US98/16387, filed Aug. 6, 1998, entitled "Novel Exendin Agonist Compounds" having the amino acid sequences of SEQ ID NOS:37-40 therein.

Exemplary exendin analogs of formula (VIII) include those wherein $Xaa_1$ is His, Tyr or 4-imidazopropionyl. More preferably, $Xaa_1$ is His or 4-imidazopropionyl.

Provided are those compounds of formula (VIII) wherein $Xaa_2$ is Gly.

Provided are those compounds of formula (VIII) wherein $Xaa_{14}$ is Leu, pentylglycine or Met.

Provided are those compounds of formula (VIII) wherein $Xaa_{25}$ is Trp or Phe.

Provided are those compounds of formula (VIII) wherein $Xaa_{27}$ is Lys or Lys-$NH^\epsilon$—R where R is Lys, Arg, $C_1$-$C_{10}$ straight chain or branched alkanoyl and $Xaa_{28}$ is Asn.

Also provided are compounds of formula (VIII) wherein $Xaa_6$ is Phe or naphthylalanine; $Xaa_{22}$ is Phe or naphthylalanine; $Xaa_{23}$ is Ile or Val and $Xaa_{31}$, $Xaa_{36}$, $Xaa_{37}$ and $Xaa_{38}$ are independently selected from Pro, homoproline, thioproline or N-alkylalanine.

According to one embodiment, $Xaa_{39}$ is Ser or Tyr. Provide are compounds wherein $Xaa_{39}$ is Ser. Preferably, Z is —$NH_2$.

According to one embodiment, provided are compounds of formula (VIII) wherein $Xaa_6$ is Phe or naphthylalanine; $Xaa_{22}$ is Phe or naphthylalanine; $Xaa_{23}$ is Ile or Val; $Xaa_{27}$ is Lys or Lys-$NH^\epsilon$—R where R is Lys, Arg, $C_1$-$C_{10}$ straight chain or branched alkanoyl, and $Xaa_{28}$ is Asn; and $Xaa_{31}$, $Xaa_{36}$, $Xaa_{37}$ and $Xaa_{38}$ are independently selected from Pro, homoproline, thioproline or N-alkylalanine.

In another embodiment, exendins and exendin analogs of the invention do not include the peptides of SEQ ID NOS:7-13. In one embodiment, exendin analogs include the analogs of Formulas (I-VIII), with the proviso that the analogs do not include the peptides of SEQ ID NOs:1-2.

Also useful in the methods provided herein are narrower genera of compounds of the disclosed formulas having peptides of various lengths, for example genera of compounds that do not include peptides having a length of 28, 29 or 30 amino acid residues, respectively, or are at least 31, 32, 33, 34, 35, 36, 37 or 38 amino acids in length.

Exendins, exendin analog agonists and exendin agonists that are peptides, described herein may be prepared through peptide purification as described in, for example, Eng, et al., *J. Biol. Chem.* 265:20259-62, 1990; and Eng, et al., *J. Biol. Chem.* 267:7402-05, 1992, which are incorporated by reference herein. Alternatively, exendins, exendin peptide agonists and exendin analog agonists may be prepared by methods known to those skilled in the art, for example, as described in Raufman, et al., *J. Biol. Chem.* 267:21432-37, 1992), which is incorporated by reference herein, using standard solid-phase peptide synthesis techniques, for example, using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with, for example, t-butyloxycarbonyl (tBoc) and fluorenylmethoxycarbonyl (Fmoc).

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: BSD-112344.1-Arg (Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His (Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−50° C. to 0° C., 1 hour). The peptide may be extracted from the resin with alternating water and acetic acid, and the filtrates lyophilized. The Fmoc-peptide resins may be cleaved according to standard methods (Introduction to Cleavage Techniques, Applied Biosystems, Inc., 1990, pp. 6-12). Peptides may also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5μ, 0.46×25 cm; Vydac). Solvents (A=0.1% TFA/water and B=0.1% TFA/$CH_3CN$) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., The Pico Tag Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Exendins, exendin analog agonists and exendin agonists that are peptides may also be prepared using recombinant DNA techniques, using methods now known in the art. See, e.g., Sambrook et al., Molecular CLONING: A LABORATORY MANUAL, 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356-377 (1986).

Exendins, exendin agonists or exendin analog agonists may be formulated into pharmaceutical compositions for administration to subjects, including humans. These pharmaceutical compositions preferably include an amount of an exendin, an exendin agonist or exendin analog agonist effective to reduce body weight in the subject, and a pharmaceutically acceptable carrier.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In one embodiment, the compositions are administered by an infusion pump or subcutaneous injection of a slow release, extended release, sustained release or long acting formulation. In one embodiment, subcutaneous injections are administered once a day; once every two, three, four, five, or six days; once per week; twice per month; once a month; every other month or every third month.

Any of the exendins, exendin agonists or exendin analog agonists may be administered in the acid or amide form. Additionally, any of the exendins, exendin agonists or exendin analog agonists may form salts with various inorganic and organic acids and bases. Such salts include, without limitation, salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include, without limititation, ammonium salts, alkali metal salts, e.g., sodium and potassium salts, and alkali earth salts, e.g., calcium and magnesium salts. Acetate, hydrochloride, and trifluoroacetate salts are particular examples. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Sterile injectable forms of the compositions of this invention may be aqueous or oleaginous suspension. These suspensions may be formulated according to techniques known in the art, using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms, including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion or a loading bolus dose followed with a maintenance dose. These compositions may be administered according to any dosage schedule described herein.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

For ophthalmic use, the pharmaceutical compositions may be formulated as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of exendin, exendin agonist or exendin analog agonist that may be combined with the carrier materials to produce a single dosage form will vary depending upon the host treated and the particular mode of administration. The compositions can be formulated so that a dosage of between 0.1-1000 pmoles/kg body weight/minute (when administered by infusion) of exendin, exendin agonists or exendin analog agonist is administered to a patient receiving these compositions. In some embodiments of the invention, the dosage is 1-10 pmoles/kg body weight/minute (when administered by infusion). In one embodiment the dosage is 0.5-2.0 pmoles/kg/min when administered by intravenous infusion. The composition may be administered as a single dose, multiple doses, or over an established period of time. In one embodiment, a long acting formulation containing about 5% of an exendin, exendin agonist, or exendin analog agonist, for example, exendin-4 is administered at a dose to deliver the equivalent of from about 3 μg/kg to less than about 100 μg/kg BID, from about 3 μg/kg to less than about 30 μg/kg BID, from about 10 μg/kg to less than about 30 μg/kg BID, or about 10 μg/kg BID of said exendin, exendin agonist or exendin analog agonist. In another embodiment, the dosage is about 2.0 mg of a long acting formulation containing about a drug load of an exendin, exendin agonist, or exendin analog agonist for example, exendin-4 sufficient to deliver the equivalent of from about 3 μg/kg to less than about 100 μg/kg BID, from about 3 μg/kg to less than about 30 μg/kg BID, from about 10 μg/kg to less than about 30 μg/kg BID, or about 30 μg/kg BID of said exendin, exendin agonist or exendin analog agonist. In additional embodiments, the dosage is about 1.0, 1.25, 1.5, 1.75, 2.25, 2.5, 2.75, 3.0, 3.25, 3.5, 3.75, 4.0, 4.25, 4.5, 4.75, or 5.0 mg of a long acting formulation containing a percent (drug load) of an exendin, exendin agonist, or exendin analog agonist for example, exendin-4 sufficient to deliver the equivalent of from about 3 μg/kg to less than about 100 μg/kg BID, from about 3 μg/kg to less than about 30 μg/kg BID, from about 10 μg/kg to less than about 30 μg/kg BID, or about 30 μg/kg BID of said exendin, exendin agonist or exendin analog agonist. It will be recognized that the exact dosage will vary with the percent exendin and the amount of carriers and/or excipients in a particular formulation. It is well within the skill of those of ordinary skill in the art to make such adjustments in order to obtain the desired plasma concentrations of an exendin, exendin agonist or exendin analog agonist described herein.

In order that the invention described herein may be more fully understood, the following examples are set forth. It should be understood that these examples are for illustrative purposes only and are not to be construed as limiting this invention in any manner.

EXAMPLES

Example 1

Reversal of Diabetes in NOD Mice Using Exenatide

Mice. NOD female mice were purchased from Taconic (Germantown, N.Y.), and housed and fed under specific pathogen-free conditions. The mice were monitored daily for diabetes onset by urine testing using Keto-Diastix (Bayer, Etobicoke, Canada). Diabetes onset was diagnosed by the presence of glucosuria (>6 mmol/l), ketonuria (>1.5 mmol/l) and a 10- to 12-h fasting blood glucose $\geq 9$ mmol/l on two consecutive days, measured on a glucose meter (Glucometer Elite; Bayer). Treatments were started within 4 to 7 days after diabetes onset in NOD mice aged 10-14 weeks old.

Analysis of pancreatic insulin content. For insulin assays, half of each pancreas was weighed, minced with fine scissors in a small beaker with 1.0 acidified ethanol (75% ethanol, 1.5% 12 mmol/l HCl, and 23.5% $H_2O$), and incubated for 24 hours at 4° C. to extract insulin from tissue. The ethanolic extracts were diluted in insulin assay buffer, and insulin was measured using a radioimmunoassay kit for rat and mouse insulin (Linco, St. Charles, Mo.).

Pancreatic histology. Half of each pancreas was fixed in 10% buffered formalin and embedded in paraffin. Serial sections 4.5 mm thick were cut. Deparaffinized sections were stained for b-cells (insulin-positive) by an immunoperoxidase technique. The sections were first incubated with a polyclonal guinea pig anti-insulin antibody (Dako, Carpenteria, Calif.), then with a biotinylated goat anti-guinea pig antibody (Vector, Burlingame, Calif.) and a strepavidin peroxidase conjugate and substrate kit (InnoGenex iso-IHC DAB kit, San Ramon, Calif.) that stained insulin-positive cells a golden brown. Coded slides were examined by light microscopy.

Results. Exenatide (3-100 μg/kg) was given s.c. twice a day for 3 weeks. Blood glucose (BG) was 12.0±0.4 mmol/L before treatment and rose to 19.5±1.0 mmol/L after 3 weeks in vehicle-treated mice. In contrast, BG decreased progressively during the 3 weeks of exenatide treatment. Normoglycemia (BG<8 mmol/L) was achieved and lasted for 13 weeks after stopping treatments in 4 of 11 mice (36%) treated with 3 μg/kg exenatide, in 6 of 12 mice (50%) treated with 10 μg/kg exenatide, and in 3 of 11 mice (27%) of mice treated with 100 μg/kg exenatide. Plasma C-peptide level was restored, and pancreative insulin content was partially restored in the NOD ice that remained normoglycemic for 13 weeks (6/12) after only 3 weeks of treatment with exenatide at 10 μg/kg. See Table 2 below. Also, pancreatic histology revealed more insulin-stained cells after exenatide treatment. In summary, a short course of exenatide treatment increased pancreatic insulin content and reverse hyperglycemia long-term in 50% of NOD mice with recent-onset diabetes without the need for concomitant immunotherapy.

TABLE 3

| Mouse | Treatment | N = | Glucose mmol/L | HbA1C % | C-peptide pmol/ml | Insulin μg/pancreas |
|---|---|---|---|---|---|---|
| NOD | Before | 5 | 12.0 ± 0.4 | 5.5 ± 0.1 | 1.52 ± 0.36 | 1.04 ± 0.25 |
| NOD | Vehicle | 9 | 28.8 ± 0.2 | 12.5 ± 0.5 | 0.02 ± 0.01 | 0.06 ± 0.02 |
| NOD | Exenatide | 6 | 6.3 ± 0.4 | 3.4 ± 0.2 | 0.52 ± 0.05 | 5.66 ± 1.13 |
| NOD-scid | None | 8 | 5.4 ± 0.2 | 3.2 ± 0.1 | 0.56 ± 0.05 | 11.81 ± 1.37 |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method to achieve sustained normoglycemia in a human with diabetes comprising administering to said human a pharmaceutical composition comprising a peptide selected from the group consisting of SEQ ID NO: 1, SEQ ID NO: 2, SEQ ID NO: 3, and SEQ ID NO: 12 for a period of time and in an amount effective to achieve normoglycemia in the human and then ceasing said administering for at least one week, whereby normoglycemia is sustained for said at least one week.

2. The method of claim 1 wherein the peptide is SEQ ID NO: 1.

3. The method of claim 1 wherein the peptide is SEQ ID NO: 2.

4. The method of claim 1 wherein the peptide is SEQ ID NO: 3.

5. The method of claim 1 wherein the peptide is SEQ ID NO: 12.

* * * * *

UNITED STATES PATENT AND TRADEMARK OFFICE
CERTIFICATE OF CORRECTION

PATENT NO. : 8,299,024 B2  
APPLICATION NO. : 12/298933  
DATED : October 30, 2012  
INVENTOR(S) : Rabinovitch et al.

Page 1 of 1

It is certified that error appears in the above-identified patent and that said Letters Patent is hereby corrected as shown below:

On the Title Page, Right Column, Item (56) OTHER PUBLICATIONS:
Line 23, delete "/specialenalish/" and insert --/specialenglish/-- therefor Signed and Sealed this
Third Day of December, 2013

Margaret A. Focarino
*Commissioner for Patents of the United States Patent and Trademark Office*